(12) United States Patent
Germann et al.

(10) Patent No.: US 6,528,276 B1
(45) Date of Patent: Mar. 4, 2003

(54) FUSION PROTEINS, DNA MOLECULES, VECTORS, AND HOST CELLS USEFUL FOR MEASURING PROTEASE ACTIVITY

(75) Inventors: Ursula Germann, Newton, MA (US); Thomas Hoock, Somerville, MA (US); Ann Kwong, Cambridge, MA (US)

(73) Assignee: Vertex Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 09/570,267

(22) Filed: May 12, 2000

Related U.S. Application Data

(62) Division of application No. 09/144,769, filed on Aug. 31, 1998, now Pat. No. 6,117,639.

(51) Int. Cl.$^7$ .............................. C12Q 1/37; C07H 2/07
(52) U.S. Cl. .............................. 435/23; 435/6; 435/7.1; 435/455; 435/465; 435/24; 536/23.1; 536/23.4; 536/23.51; 536/23.7; 536/23.72; 530/350
(58) Field of Search .............................. 435/6, 7.1, 455, 435/465, 23, 24; 536/23.1, 23.4, 23.51, 23.7, 23.72; 530/350

(56) References Cited

U.S. PATENT DOCUMENTS

| | | | |
|---|---|---|---|
| 5,599,906 A | * | 2/1997 | Dasmahaptra .............. 530/350 |
| 5,861,267 A | * | 1/1999 | Su .............................. 435/23 |

FOREIGN PATENT DOCUMENTS

| | | | |
|---|---|---|---|
| EP | 0 421 109 A2 | 4/1991 | ............ C12Q/1/37 |
| WO | WO 91/16436 | 10/1991 | ........... C12N/15/62 |
| WO | WO 93/01305 | 1/1993 | ............ C12Q/1/02 |
| WO | WO 95/02065 | 1/1995 | ............ C12Q/1/00 |
| WO | WO 96/37609 | 11/1996 | ........... C12N/15/12 |
| WO | WO 97/38117 | 10/1997 | ........... C12N/15/85 |
| WO | WO 98/41866 | * 9/1998 | |

OTHER PUBLICATIONS

Bimalendu Dasmahapatra, et al., "A Genetic System for Studying the Activity of a Proteolytic Enzyme,"*Proc. Natl. Acad. Sci.*, 89, pp. 4159–4162 (1992).

Yuji Hirowatari, et al., "A Novel Method for Analysis of Viral Proteinase Activity Encoded by Hepatitis C Virus in Cultured Cells," *Analytical Biochemistry*, 225, pp. 113–120 (1995).

D. Latchman, "Eukaryotic Transcription Factors," Academic Press, San Diego, pp. 81–89, 95–99, 271–273, 298 (1995).

Michael G. Murray, et al., "Inactivation of a Yeast Transactivator by the Fused HIV–1 Proteinase: a Simple Assay for Inhibitors of the Viral Enzyme Activity," *Gene*, 134, pp. 123–128 (1993).

David No, et al., "Ecdysone–Inducible Gene Expression in Mammalian Cells and Transgenic Mice," *Proc. Natl. Acad. Sci.*USA, 93, pp. 3346–3351 (1996).

Tracy A. Smith, et al., "Direct Selection for Sequences Encoding Proteases of Known Specificity," *Proc. Natl. Acad. Sci.*, 88, pp. 5159–5162 (1991).

\* cited by examiner

*Primary Examiner*—Rebecca E. Prouty
(74) *Attorney, Agent, or Firm*—Fish & Neave; James F. Haley, Jr.

(57) ABSTRACT

The present invention relates to novel fusion proteins, DNA molecules encoding the same, vectors comprising the DNA molecules, and host cells containing the vectors for use in measuring protease activity using a novel transcriptional assay. This invention also relates to a method for determining the inhibitory activity of a compound against a protease and to a method for comparing the activity of two proteases which recognize the same cleavage site. Kits for assaying protease activity comprising DNA molecules encoding the fusion protein substrates of this invention are also contemplated.

15 Claims, 9 Drawing Sheets

Control Plasmids:

pSRα pSRα-NS3-4A(S1165A)

US 6,528,276 B1

FUSION PROTEINS, DNA MOLECULES, VECTORS, AND HOST CELLS USEFUL FOR MEASURING PROTEASE ACTIVITY

This application is a divisional of U.S. application Ser. No. 09/144,769, filed Aug. 31, 1998, now U.S. Pat. No. 6,117,639.

TECHNICAL FIELD OF THE INVENTION

The invention relates to fusion proteins, DNA molecules encoding the fusion proteins, vectors comprising the DNA molecules, host cells transformed with the vectors, and methods and kits for using them to determine the activity of a protease. Specifically, the invention relates to a fusion protein having a protease cleavage site, a ligand-binding domain, and a DNA-binding domain, wherein (1) the association of a ligand with the ligand-binding domain of said fusion protein mediates the binding of the DNA-binding domain of said fusion protein to a ligand-response element ("LRE") that is operatively linked to a reporter gene; and wherein (2) the fusion protein comprises an expression modulator domain or associates with a second protein having an expression modulator domain, wherein said expression modulator domain regulates transcription of the reporter gene. The invention also relates to kits for assaying protease activity comprising DNA molecules encoding the fusion proteins, an appropriate ligand, and DNA molecules comprising a promoter-reporter gene construct and at least one LRE recognized by the DNA binding domain of the fusion protein. The DNA molecules in these kits may be isolated or present in host cells.

BACKGROUND OF THE INVENTION

Proteases play an important role in the regulation of biological processes in almost every life form from bacteria to virus to mammals. They perform critical functions in, for example, digestion, blood clotting, apoptosis, activation of immune responses, zymogen activation, viral maturation, protein secretion and protein trafficking.

Proteases have been implicated as the cause of or as contributors to several diseases such as Alzheimer's disease, cystic fibrosis, emphysema, hypertension, tumor invasion and metastasis and viral-associated diseases [e.g., Kim, T. W., et al., (1997) "Alternative Cleavage of Alzheimer-associated Presinilins During Apoptosis by a Caspase-3 Family Protease," *Science* 277:373–6; Lacana, E. et al., (1997) "Disassociation of Apoptosis and Activation of IL-1 beta-converting Enzyme/Ced-3 Proteases by ALG-2 and the Truncated Alzheimer's gene ALG-3," *J. Immunol.* 158:5129–35; Birrer, P., (1995) "Proteases and Antiproteases in Cystic Fibrosis: Pathogenic Considerations and Therapeutic Strategies," *Respiration* 62:25–8; Patel, T., et al., (1996) "The Role of Proteases During Apoptosis," *FASEB J.* 10:587–97].

Several viral genomes also encode proteases that are important in the viral maturation process. For example, the viral aspartyl protease of the Human Immunodeficiency Virus (HIV) cleaves a HIV polypeptide containing the Gag and Pol polyproteins.

In another example, the hepatitis C virus (HCV) produces a long polypeptide translation product, NH2-C-E1-E2-p7-NS2-NS3-NS4A-NS4B-NS5A-NS5B-COOH, which is cleaved to produce at least 10 proteins. C, E1 and E2 are putative structural proteins, and the remainder are known as the nonstructural (NS) proteins. One of those proteins is NS3, a 70 kilodalton protein having serine protease activity.

It is been shown that the protease activity of NS3 resides exclusively in the N-terminal 180 amino acids of the enzyme. The NS3 protease cleavages at four sites in the nonstructural region of the HCV polypeptide (3/4A, 4A/4B, 4B/5A, and 5A/5B). Another protein, NS4A, has 54 amino acids and has been characterized as a cofactor for the NS3 protease [C. Failla, et al., (1994) *J. Virology* 68:3753–3760]. The C-terminal 33 amino acids of NS4A are required for cleavage at the 3/4A site and 4B/5A sites and accelerate the rate of cleavage at the 5A/5B site. Several other NS3 serine protease-dependent cleavage site sequences have been identified in various strains of HCV [A. Grakoui, et al., (1993) *J. Virology* 67:2832–2843 incorporated by reference herein].

The ability to detect viral, cellular, or microorganism protease activity in a quick and simple assay is important in the biochemical characterization of these proteases, in detecting viral infection, and in the screening and identification of potential inhibitors.

Several protease assays are known in the art. T. A. Smith et al., *Proc. Natl. Acad. Sci. USA*, 88, pp. 5159–62 (1991); B. Dasmahapatra et al., *Proc. Natl. Acad. Sci. USA*, 89, pp. 4159–62 (1992); and M. G. Murray et al., *Gene*, 134, pp. 123–128 (1993) each describe protease assay systems utilizing the yeast GAL4 protein. Each of these documents describe inserting a protease cleavage site in between the DNA binding domain and the transcriptional activating domain of GAL4. Cleavage of that site by a coexpressed protease renders GAL4 transcriptionally inactive leading to the inablility of the transformed yeast to metabolize galactose.

Y. Hirowatari et al., *Anal. Biochem.*, 225, pp. 113–120 (1995) describes an assay to detect HCV protease activity. In this assay, the substrate, HCV protease and a reporter gene are cotransfected into COS cells. The substrate is a fusion protein consisting of (HCV NS2)(DHFR)-(HCV NS3 cleavage site)-Tax1. The reporter gene is chloramphenicol transferase (CAT) under control of the HTLV-1 long terminal repeat (LTR) and resides in the cell nucleus following expression. The uncleaved substrate is expressed as a membrane-bound protein on the surface of the endoplasmic reticulum due to the HCV NS2 portion. Upon cleavage, the released Tax1 protein translocates to the nucleus and activates CAT expression by binding to the HTLV-1 LTR. Protease activity is determined by measuring CAT activity in a cell lysate.

Each of the assays described above requires simultaneous (1) expression of an active protease and a substrate and (2) transcription of a reporter gene construct. The constitutive nature of these assays can often produce uncontrollable and undesirable effects. These effects may give rise to misleading or inaccurate conclusions regarding the activity of the protease. Thus, there is a need for a sensitive and quantitative protease assay that is inducible or can be readily controlled by the user.

SUMMARY OF THE INVENTION

The present invention fulfills this need by providing novel fusion proteins, DNA molecules encoding them, vectors comprising the DNA molecules, and host cells containing the vectors useful in a fusion protein ligand-dependent transcriptional assay to determine the activity of a protease.

The novel fusion protein comprises a protease cleavage site, a ligand-binding domain, and a DNA-binding domain, wherein (1) the association of a ligand with the ligand-binding domain of said fusion protein mediates the binding of the DNA-binding domain of said fusion protein to a LRE that is operatively linked to a reporter gene; and wherein (2) the fusion protein comprises an expression modulator domain or associates with a second protein having an expression modulator domain, wherein said expression modulator domain regulates the transcription of the reporter gene.

According to the methods of this invention, the binding of a ligand to the ligand binding domain of the uncleaved fusion protein initiates the activation or repression of transcription of the reporter gene at a discrete point in time. This inducibility allows the assay to be better controlled and therefore, produces more accurate results.

Cleavage of the fusion protein at the protease cleavage site deregulates transcription of the reporter gene by preventing the expression modulator domain from modulating transcription positively or negatively. The amount of cleaved fusion protein is quantitated by assaying an increase or decrease in transactivation of a reporter gene, whose expression is driven by a promoter which is modulated by the expression modulating domain of the fusion protein.

This invention also relates to a method for measuring the inhibitory activity of a compound against a protease comprising the steps of incubating the fusion protein with a protease in the presence or absence of a compound whose activity is being tested, adding a ligand to the incubation and quantifying the gene product produced from a reporter gene.

Yet another embodiment of this invention relates to a method for comparing the activity of two proteases or mutants of a protease which recognize the same cleavage site.

The Invention also relates to kits for assaying protease activity comprising DNA molecules encoding the fusion protein, the fusion protein or host cells containing the DNA molecules, wherein the kit optionally includes DNA molecules encoding a protease, DNA molecules comprising a reporter gene whose expression is regulated by said fusion protein, a ligand which associates and regulates the activity of said fusion protein, and instructions for using said kit. Preferably, the DNA molecules in the kit have been engineered into a vector that allows their expression. A kit according to this invention, may comprise any one or all of the following DNA molecules transformed into a single host cell selected from the group consisting of: a DNA molecule encoding a fusion protein of this invention, a DNA molecule encoding a protease, a DNA molecule encoding a protein binding partner for the fusion protein and a DNA molecule comprising a promoter-reporter gene construct.

DETAILED DESCRIPTION OF THE INVENTION

Figure 1:
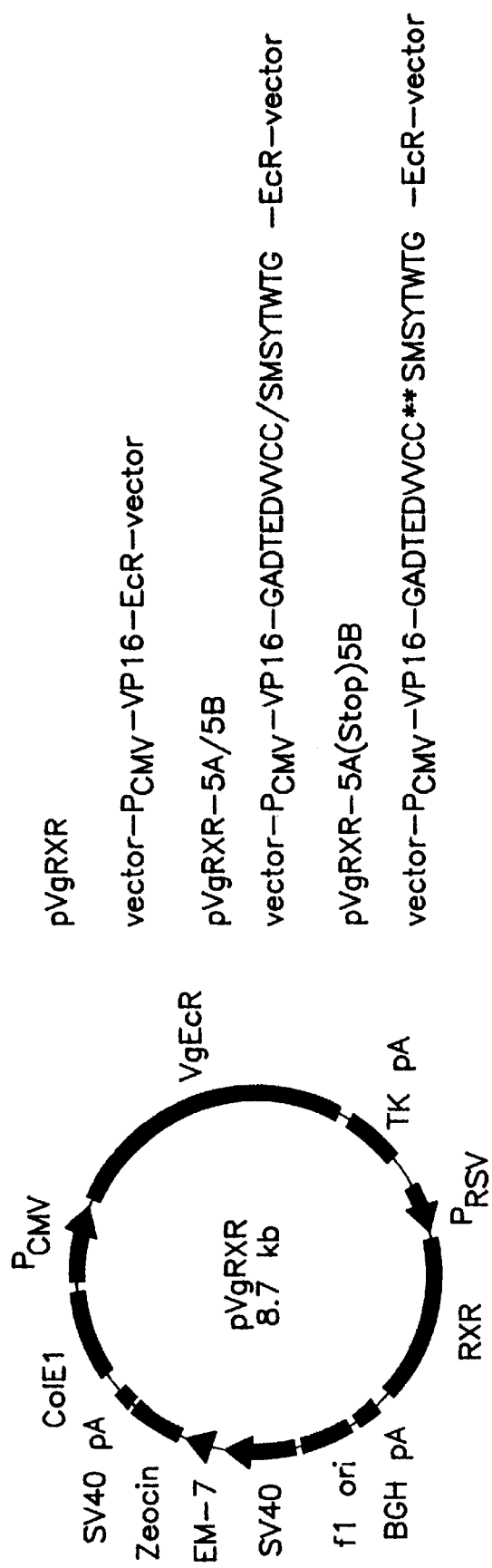
FIG. 1 depicts the structure of the vectors pVgRXR (SEQ ID NO:17), pVgRXR-5A/5B (SEQ ID NO:19), and pVgRXR-5A(Stop)5B (SEQ ID NO: 21). The backslash positioned between the cysteine and the serine of the pVgRxR-5A/5B encoded protein indicates where the cleavage will take place. The two asterisks near the cleavage site of the VgRXR-5A(Stop)5B encoded protein indicate the placement of two stop codons.

The present invention provides novel tools and methods for measuring protease activity. The activity of a protease is measured by using a novel fusion protein as a substrate in a transcriptional assay wherein transcription is activated or repressed at a discrete time point by addition of a ligand after a protease and a fusion protein of this invention are incubated together.

The present invention provides a fusion protein comprising: a protease cleavage site, a ligand binding domain, and a DNA binding domain, wherein (1) the association of a ligand with the ligand-binding domain of said fusion protein mediates the binding of the DNA-binding domain of said fusion protein to a ligand response element ("LRE") operatively linked to a reporter gene; and wherein (2) the fusion protein comprises an expression modulator domain or associates with a second protein having an expression modulator domain, wherein said expression modulator domain regulates transcription of the reporter gene.

A protease cleavage site (hereinafter, "PCS") according to this invention is a peptide incorporated into the primary sequence of the fusion protein of this invention. It may be located in any of the DNA binding domain, ligand binding domain, or, optionally, the expression modulator domain, if one exists, of the protein, as well as in between any two of these domains.

The presence of the cleavage site in the protein should not substantially interfere with the activity of the fusion protein's DNA binding domain, ligand binding domain, or, if present, expression modulator domain.

To ensure that the protease cleavage site does not substantially interfere with the activity of the above domains of the fusion protein, the activity of a fusion protein with the PCS may be compared with the activity of the same fusion protein without the PCS by gel shift assay to assess DNA binding or by transcriptional assay (e.g., D. Latchman, (1995) *Eukarvotic Transcription Factors*, 2nd Ed. Academic Press:London).

Also, the protease cleavage site should be engineered into the fusion protein such that, when cleaved, neither of the resulting fusion protein fragments are capable of modulating the expression of a target or reporter gene.

Preferably, there is only one target protease cleavage site located within the fusion protein substrate.

According to a preferred embodiment, the protease cleavage site is situated between the DNA binding domain and the effector modulator domain of the fusion protein.

In a preferred embodiment of this invention, the PCS has an amino acid sequence comprising a processing/protease cleavage site in the HIV gag and gag/pol polyproteins or in the HCV polyprotein. In a more preferred embodiment of this invention the HIV PCS site selected from the group consisting of Seq ID Nos. 1–10 [S. Pichuantes, et al., (1989) "Recombinant HIV1 Protease Secreted by Saccharomyces cervisiae Correctly Processes Myristylated gag Polyprotein," *Proteins: Structure, Function, and Genetics* 6:324–337 is incorporated by reference.] In a more preferred embodiment of this invention, the PCS has the amino acid sequence of a cleavage site for the HCV NS3 serine protease or HIV aspartyl protease. In a still more preferred embodiment of this invention the PCS has the amino acid sequence of an HCV 5A/5B protease cleavage site. In a still more preferred embodiment of this invention, the 5A/5B protease cleavage site is Seq ID No. 10.

The next portion of the fusion protein of this invention is the ligand binding domain (hereinafter, "LBD"). The LBD is a peptide domain which binds to a ligand, wherein said ligand binding is required for said fusion protein to (1) bind to a LRE, wherein the element is operatively linked to a reporter gene; and/or (2) to bind to a protein binding partner as an interim step preceding the binding to the resulting fusion protein-protein binding partner complex to a LRE. Thus, ligand binding to the fusion protein ligand binding domain is necessary for the transcriptional regulation of the expression of said reporter gene.

Ligand binding domains suitable for use in this invention may be derived from ligand binding domains of transcription factors that initiate or repress of transcription upon ligand binding. Such transcription factors include hormone receptors [Freedman, L. P., 1998, "Molecular Biology of Steroid and Nuclear Hormone Receptors," *Progress in Gene Expression*, Boston: Birkhauser; Tsai, M-J., 1994, "Mechanism of Steroid Hormone Regulation of Gene Transcription," *Molecular Biology Intelligence Unit*, Austin: R. G. Landes Co.; Eggert, M. et al., "The Glucocorticoid Hormone Receptor," *Inducible Gene Expression, vol. 2* (1995) Birkhauser: Boston, Mass. Ed. P. A. Baeuerle. pp. 131–156; Piedrafita, F. J. and M. Pfahl, "The Thyroid Hormone Receptors," *Inducible Gene Expression, vol. 2* (1995) Birkhauser: Boston, Mass. Ed. P. A. Baeuerle. pp. 157–185; Keaveney M. and H. G. Stunnenberg, "Retinoic Acid Receptors," *Inducible Gene Expression, vol. 2* (1995) Birkhauser: Boston, Mass. Ed. P. A. Baeuerle. pp. 187–242), each of which is herein incorporated by reference]; carbohydrate-responsive transcription factors; metallothionein (MT) genes; orphan receptors; tetracycline-inducible transcription factors; the IPTG-inducible transcription factors; dioxin receptors; and aryl hydrocarbon receptors.]

In a preferred embodiment of this invention, the ligand binding domain is derived from the ligand binding domains of the steroid/thyroid hormone receptor superfamily. Amino acid sequences encoding steroid and nuclear receptor ligand binding domains are well known in the art [See, for example, S. Simons, (1998) "Structure and Function of the Steroid and Nuclear Receptor Ligand Binding Domain," *Molecular Biology of Steroid and Nuclear Hormone Receptors: Progress in Gene Expression*, Birkhauser: Boston, Mass., the disclosure of which is herein incorporated by reference]. In a more preferred embodiment, the ligand binding domain is derived from an ecdysone receptor.

In a further embodiment of this invention, a ligand binding domain from a transcription factor may be modified in the fusion protein of this invention such that it binds to a different ligand. For example, a human progesterone receptor ligand binding domain may be mutated so that it is capable of binding the anti-progesterone compound RU486 (Wang, Y., et al., (1997) "Positive and Negative Regulation of Gene Expression in Eukaryotic Cells with an Inducible Transcriptional Regulator," *Gene Ther*. 4:432–41, the disclosure of which is herein incorporated by reference). Such RU486-inducible GAL4 DNA binding domain fusion protein is contemplated for use in this invention.

A DNA binding domain (hereinafter, "DBD") refers to a peptide sequence in the fusion protein according to this invention which recognizes and binds to a specific nucleotide sequence (e.g., a DNA element or a LRE). DNA binding domains useful according to this invention may be derived from the DNA binding domains of DNA binding proteins, such as transcription factors.

In a preferred embodiment, these DNA binding proteins are transcription factors that directly bind DNA and initiate or repress transcription. Such transcription factors are well known in the art [McKnight, S. L. and K. R. Yamamoto, 1992, "Transcriptional Regulation," *Cold Spring Harbor Monograph Series*, Plainview, N.Y.: Cold Spring Harbor Laboratory Press; Latchman, D. S., 1995, *Eukarvotic Transcription Factors*, San Diego: Academic Press, 2.ed.; Latchman, D. S., 1993, "Transcription Factors: A Practical Approach," *The Practical Approach Series*, New York: IRL Press at Oxford University Press; Papavassiliou, A., (1997) "Transcription Factors in Eukaryotes," *Molecular Biology Intelligence Unit*, New York: Chapman & Hall; Eckstein, F., and D. M. J. Lilley, 1997, "Mechanisms of Transcription," *Nucleic Acids and Molecular Biology*, Vol. 11, New York: Springer-Verlag, the disclosures of which are herein incorporated by reference].

Preferred DNA binding domains contemplated for use in this invention include the DNA binding domains of the following transcription factors: homeobox proteins, zinc finger proteins (Sluyser, M., 1993, *Zinc Finger Proteins in Oncogenesis: DNA Binding and Gene Regulation*, New York: New York Academy of Sciences), helix-turn-helix proteins, helix-loop-helix proteins (e.g., Littlewood, Trevor D., 1998, *Helix-Loop-Helix Transcription Factors*, 3rd. Ed., New York: Oxford University Press), leucine zipper proteins (e.g., Hurst, H. C., 1996, *Leucine Zippers: Transcription Factors*, 3rd. ed., San Diego: Academic Press), GAL4 protein, hormone receptors, orphan receptors, and *E.coli* transcription factors such as the lactose operon repressor, tetracycline-controlled transactivator, and FadR.

The present invention also contemplates the use of the DBD's of metal-binding DNA-binding proteins that regulate the transcription of metallothionein (MT) genes. Such metal-binding DNA-binding proteins include MTF-1, ACE1, and AMT1. [Heuchel, R., et al., "Transcriptional Regulation by Heavy Metals, Exemplified at the Metallothionein Genes," *Inducible Gene Expression. vol.* 1 (1995) Birkhauser: Boston, Mass. Ed. P. A. Baeuerle. pp. 206–240.]

In a more preferred embodiment of this invention, the DNA-binding domain is obtained from a member of the steroid/thyroid superfamily of receptors. The members of the steroid/thyroid superfamily of receptors are known in the art as hormone binding proteins that function as ligand-dependent transcription factors. They include identified members of the steroid/thyroid superfamily of receptors for which specific natural ligands have not yet been identified (referred to herein as "orphan receptors") [B. M. Forman, (1998) "Orphan Nuclear Receptors and Their Ligands," *Molecular Biology of Steroid and Nuclear Hormone Receptors*, L. P. Freedman, Ed., Birhauser: Boston, pp. 281–305.]

Members of the orphan receptors useful in this invention include HNF4, the COUP family of receptors and COUP-like receptors, peroxisome proliferator-activated receptors (PPARs), insect derived knirps and knirps-related receptors, and various isoforms thereof.

The amino acid sequences encoding such DBD's are well known in the art [F. Rastinejad, (1998) "Structure and Function of the Steroid and Nuclear Receptor DNA Binding Domains," *Molecular Biology of Steroid and Nuclear Hormone Receptors: Progress in Gene Expression* Birkhauser: Boston, Mass., the disclosure of which is herein incorporated by reference].

Figure 2:
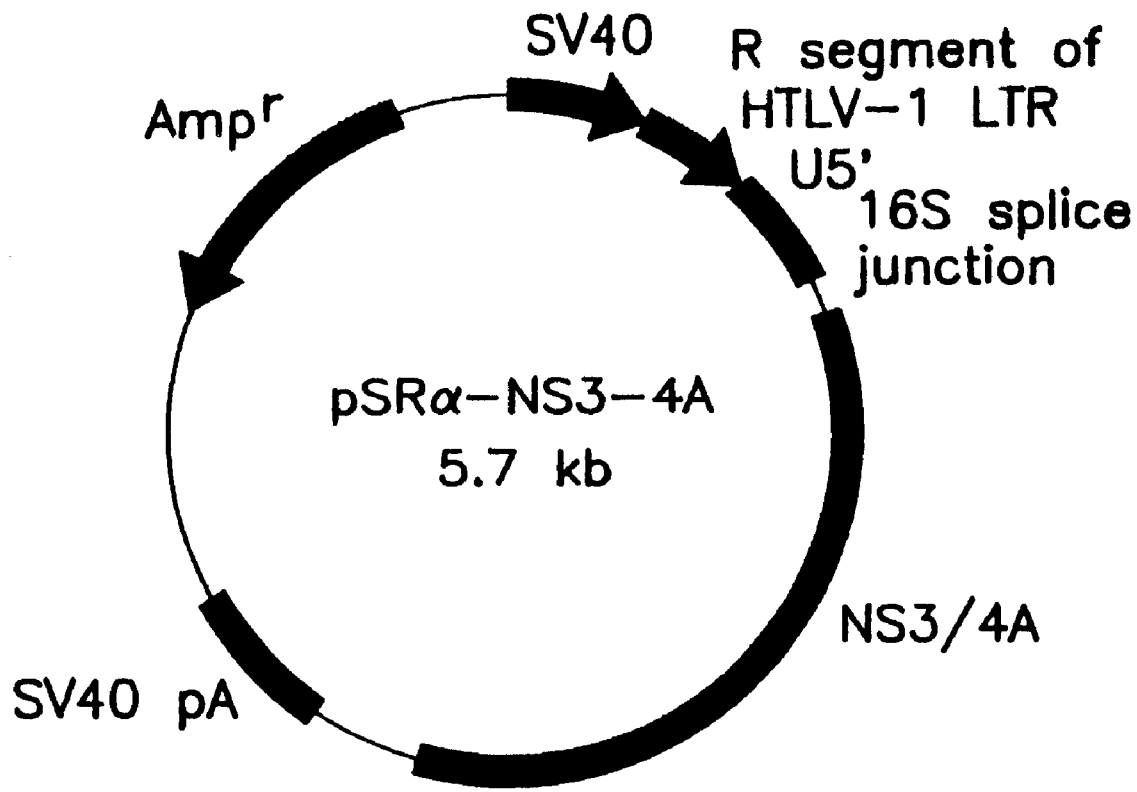
FIG. 2 depicts the structure of a DNA vector encoding the HCV NS3-4A protease, pSRα-NS3-4A.

Like the LBD used in the fusion proteins of this invention, the DNA binding domains of this invention may be modified from the sequence present in the source transcription factor so that it recognizes a different LRE. For example, the amino acid sequence of the DNA binding domain of a steroid/thyroid family members may be modified such that the DNA binding domain binds to a LRE recognized by another steroid/thyroid family member. For example, modification of the "P-box" amino acid sequence of a steroid/thyroid family member, i.e., a region in the DNA-binding domain that is typically located at the junction of the first zinc finger and the linker region, is contemplated by this invention (Umesono et al., (1989) *Cell* 57:1139–1146, particularly FIG. 2 and Table 1; the disclosure of which is herein incorporated by reference).

In a preferred embodiment, the DNA binding domain is derived from the Drosophila ecdysone receptor, wherein the P-box of the ecdysone receptor having the amino acid sequence EGCKG (SEQ. ID. NO. 23) is replaced with the amino acid sequence GSCKV (SEQ. ID. NO. 24). The new P-box sequence GSCKV causes the ecdysone receptor to recognize the LRE -AGAACA- instead of the LRE -AGGTCA-.

Members of the steroid/thyroid superfamily of receptors that are particularly useful for providing the LBD and/or the DBD of a fusion protein of this invention include steroid receptors such as the glucocorticoid receptor (GR), the mineralcorticoid receptor (MR), the estrogen receptor (ER), the progesterone receptor (PR) such as hPR-A or hPR-B, the androgen receptor (AR), the vitamin D3 receptor (VDR); retinoid receptors such as retinoic acid receptors (e.g., RARα, RARβ, or RARγ) and retinoid X receptors (e.g., RXRα, RXRβ, or RXRγ); thyroid receptors (TR) such as TRα and TRβ; insect-derived receptors such as the ecdysone receptors; and isoforms thereof.

According to one preferred embodiment, a fusion protein of this invention contains a DNA binding domain which is engineered near or next to a ligand binding domain and neither of the two domains contains a PCS, nor is a PCS located between the two domains.

An optional component of the fusion protein of this invention is an expression modulator domain. As stated above, if the expression modulator domain is not present on the fusion protein, it must be present on a protein that associates with the fusion protein.

Expression modulator domains contemplated for use in this invention, either as part of the fusion protein or a separate protein which associates with the fusion protein, are typically derived from DNA binding proteins, such as transcription factors. These sequences are known in the art to activate or to repress transcription through their interaction with other transcription factors necessary for transcription.

In embodiments where the expression modulator domain is present within a second protein that binds to the fusion protein, that second protein should not increase or decrease transcription in the absence of a fusion protein of this invention and its ligand. In embodiments where the expression modulator domain is present within the fusion protein it is preferably located at the terminus opposite to the location of the DNA binding domain.

In a preferred embodiment of this invention, the expression modulator domain activates transcription as opposed to repressing that activity. Such activation domains include the N-terminal regions encoding activation domains in the steroid/thyroid superfamily of receptors, the activation domains of viral transcription factors, the yeast GCN4 activation domain or the GAL4 activation domain [K. Struhl, "Yeast GCN4 Transcriptional Activator Protein," *Transcriptional Regulation*, Eds. S. L. McKnight and K. R. Yamamoto, Cold Spring Harbor Laboratory Press (1992), pp. 833–859; A. A. F. Gann et al., "GAL11, GAL11P, and the Action of GAL4," *Transcriptional Regulation*, Eds. S. L. McKnight and K. R. Yamamoto, Cold Spring Harbor Laboratory Press (1992), pp. 931–946; K. J. Martin and M. R. Green, "Transcriptional Activation by Viral Immediate-Early Proteins: Variations on a Common Theme," *Transcriptional Regulation*, Eds. S. L. McKnight and K. R. Yamamoto, Cold Spring Harbor Laboratory Press (1992), pp. 695–725, the disclosures of which are herein incorporated by reference].

In another preferred embodiment, the expression modulating domain is part of the fusion protein. An even more preferred is when the expression modulating domain is the N-terminal activation domain of the VP16 protein.

It should be understood that the ligand binding domain, DNA binding domain and expression modulator domain need not be derived from the same transcription factor.

For example, a chimera comprising the DNA-binding domain of the retinoic acid receptor and the ligand-binding domain of the vitamin D receptor (VDR) may be made (Pemrick, S., et al., (1998) "Characterization of the Chimeric Retinoic Acid Receptor RARα/VDR," *Leukemia* 12:554–562) or a chimera comprising the Jun DNA binding domain may be fused to the estrogen receptor ligand binding domain and expression modulator activation domain (Kruse, U., et al., (1997) "Hormone-regulatable Neoplastic Transformation Induced by a Jun-Estrogen Receptor Chimera," *PNAS USA* 94:12396–12400).

Other examples include the fusion of the lacR DNA-binding domain and the VP16 activation domain. This creates a fusion protein that requires IPTG to bind to the LRE, lacO [Labow, M. et al., (1990) *Mol. Cell. Biol.* 10:3343–3356]. In another example, the fusion of the tetR protein and the VP16 activation domain creates a fusion protein which releases from the LRE, tetO, in the presence of tetracycline in cells and in transgenic animals [Gossen, M. and H. Bujard, (1992) "Tight Control of Gene Expression in Mammalian Cells by Tetracycline-Responsive Promoters," *PNAS USA* 89:5547–5551; Furth, P. A., et al., (1994) "Temporal Control of Gene Expression in Transgenic Mice by a Tetracycline-Responsive Promoter," *PNAS USA* 89:9302–9306]. A tetR-VP16 fusion protein according to this invention may contain a protease cleavage site in its DNA binding domain such that DNA binding is eliminated when the PCS is cleaved. Thus, upon addition of tetracycline, uncleaved fusion protein would continue to transactivate from tetO, whereas cleaved fusion proteins would be inactive.

A preferred embodiment of this invention is the fusion of the VP16 activation domain of herpes simplex virus, the ligand binding domain of a steroid/thyroid receptor superfamily member and the DBD of a steroid/thyroid receptor superfamily member. In a more preferred embodiment, the steroid/thyroid receptor superfamily member is the ecdysone receptor.

As described above, the invention also contemplates fusion proteins which require contact with a protein binding partner ("PBP") in order to bind DNA or to increase specificity of binding or affinity of binding of the fusion protein to its LRE. Thus, a protein binding partner according to this invention is a protein that binds to a fusion protein of this invention and increases the affinity or specificity of binding of the DNA-binding domain of the fusion protein to a specific LRE. The protein binding partner is a protein that also binds to a particular DNA element that is operatively linked to the reporter gene. If the fusion protein of this invention requires a protein binding partner for increased affinity or specificity of DNA binding, then it is desirable to ensure that the fusion protein includes a dimerization domain for interaction with the PBP.

Protein binding partners that may be suitable for interacting with the dimerization domains of the fusion proteins of this invention are known in the art. [e.g., T. D. Littlewood and G. I. Evan (1998) "Structure/Function Relationships of HLH Proteins," *Helix-Loop-Helix Transcription Factors*, 3rd. Ed., New York: Oxford University Press, pp. 27–41; Hurst, H. C., 1996, *Leucine Zippers: Transcription Factors*, 3rd. ed., San Diego: Academic Press, pp. 27–29; and L. P. Freedman, Ed., (1998) *Molecular Biology of Steroid an Nuclear Hormone Receptors: Progress in Gene Expression*, Birkhauser: Boston, Mass.].

For example, several heterodimeric partners of basic-helix-loop-helix (bHLH) transcription factors are known in the art. [Littlewood, Trevor D.., 1998, *Helix-Loop-Helix Transcription Factors*, 3rd. Ed., New York: Oxford University Press) pp. 37–41] In a more specific example, bHLH transcription factors such as the ligand-dependent dioxin receptors and aryl hydrocarbon receptors (AHRs) heterodimerize with the AHR nuclear translocator protein (ARNT) [Whitelaw, M. L. et al., (1994) "Identification of Transactivation and Repression Functions of the Dioxin Receptor and Its Basic Helix-Loop-Helix/PAS Partner Factor Arnt: Inducible Versus Constitutive Modes of Regulation," *Mol. Cell. Bio.* 14:8343–8355].

Another example is the steroid/thyroid family of receptors which have the ability to heterodimerize with each other or with other non-steroid/thyroid receptor family members (e.g., Rhee, et al., (1995) "Retinoid X-Receptor-alpha and Apolipoprotein AI Regulatory Protein 1 Differentially Modulate 3,5,3'-Triiodothyronine-Induced Transcription," *Endocrinology* 136:2697–704; Li, et al., (1997) "Coexpression of Nuclear Receptors Partners Increases Their Solubility and Biological Activities," *PNAS USA* 94:2278–83).

Yet another example are the bZIP factors which heterodimerize with several other proteins. [e.g., H. C. Hurst, *Leucine Zippers: Transcription Factors*, 3rd Ed. London: Academic Press, (1996), page, 28.]

Such heterodimers and homodimers comprising a fusion protein of this invention are contemplated.

In a preferred embodiment of this invention, a P-box modified ecdysone receptor heterodimerizes with mammalian RXR.

A fusion protein of this invention for use in cellular transcription assays should localize to the nucleus of the host cell. A nuclear localization signal already present within a domain of a fusion protein of this invention may provide the nuclear localization signal. Alternatively, a nuclear localization signal known in the art may be engineered into the fusion protein to ensure nuclear localization. [e.g., D. B. DeFranco, (1998) "Subcellular and Subnuclear Trafficking of Steroid Receptors," *Molecular Biology of Steroid and Nuclear Hormone Receptors: Proaress in Gene Expression*, Birkhauser: Boston, Mass.; Guiochon-Mantel A, et al., (1996) "The Ernst Schering Poster Award. Intracellular Traffic of Steroid Hormone Receptors," *J. Steroid Biochem. Mol. Biol.* 56:3–9, the disclosures of which are herein incorporated by reference].

In an alternative embodiment of the methods of this invention, the fusion protein lacks a ligand binding domain. Specifically, in this embodiment, the fusion protein comprises (1) a DNA-binding domain and (2) a protease cleavage site. In these methods, the transcriptional activity of the fusion protein is inducible by altering the temperature of the transcription environment or causing stress to the cells in which the transcription event takes place. For example, high affinity binding of a heat shock factor ("HSF") to its response element, HSE, is dependent on a heat shock stimulus. [e.g., J. Lis and C. Wu, "Heat Shock Factor," *Transcriptional Regulation*, Eds. S. L. McKnight and K. R. Yamamoto, Cold Spring Harbor Laboratory Press (1992), pp. 907–930; D. S. Latchman, "Transcription Factors and Inducible Gene Expression," *Eukarytic Transcription Factors*, 2nd Ed. London: Academic Press Limited, (1995) pp. 71–78.]

A protease cleavage site of interest may be engineered into the HSF protein such that the transcriptional activity of the cleaved HSF fusion protein is lower or negligible compared to uncleaved HSF fusion protein after stimulus by heat.

The use of the fusion proteins, DNA molecules and vectors of this invention contemplated by the methods of this invention include cellular and in vitro transcription reactions.

Methods for conducting transcription assays in cells are known. [e.g., R. White and M. Parker, "Analysis of Cloned Factors," *Transcription Factors: A Practical Approach*, Ed. D. S. Latchman, IRL Press: Oxford (1993) pp. 145–152; F. M. Ausubel et al., Eds. *Current Protocols in Molecular Biology*, Greene Publishing Associates & Wiley-Interscience: New York (1991); Sambrook et al. *Molecular Cloning: A Laboratory Manual* 2nd. Ed., Cold Spring Harbor Laboratory Press (1989)]. Briefly, DNA encoding a fusion protein of this invention, a reporter plasmid, a protease and, optionally, a second protein having a expression modulator domain will be introduced into a cell. Next, the transcriptional activity of the fusion protein will be induced by adding a ligand or by altering the environment of the cell (e.g., changing the temperature of the environment of the cell). The quantity of mRNA, the quantity of reporter protein, or the activity of the reporter protein will be measured using standard techniques known in the art. Transcription in the absence of protease can be compared with transcription in the presence of protease.

Methods for conducting in vitro transcription reactions are also known [Sierra, F., et al., "In vitro Transcription with Nuclear Extracts from Differentiated Tissues," *Gene Transcription: A Practical Approach* (1993) Oxford University Press: Walton Street, Oxford. Ed. D. Hames and S. Higgins. pp. 125–152; Snoek, R. et al., (1996) "Induction of Cell-Free, In Vitro Transcription by Recombinant Androgen Receptor Peptides," *J. Steroid Biochem. Molec. Biol.* 59:243–250; Dignam, J. D., et al., (1992) "Preparation of Nuclear and Cytoplasmic Extracts from Mammalian Cells," *In Current Protocols in Molecular Biology* (Ed. by F. A. Ausubel et al.) John Wiley and Sons: New York pp. 12.1.1–12.1.9.; Klein-Hitpass, L., et al., (1990) "The Progesterone Receptor Stimulates Cell-Free Transcription by Enhancing the Formation of a Stable Preinitiation Complex," *Cell* 60:247–257].

Briefly, cellular extracts prepared by protocols which have been shown to support in vitro transcription reactions would be prepared. Purified or partially purified proteins would be added to the cellular extract together with a reporter plasmid. Such purified or partially purified proteins, such as the fusion protein of this invention may be produced by overexpression in a cell introduced to the DNA encoding the fusion protein, e.g., SF9 cells via baculovirus infection, plant cells, yeast cells, mammalian cells, and bacterial cells. Proteins such as the protease and, optionally, the second protein having an expression modulator domain and/or a protein binding partner may also be prepared from their original sources using methods known in the art to purify them.

Next, the transcriptional activity of the fusion protein will be induced by adding a ligand. The quantity of mRNA produced, the quantity of reporter protein produced, or the activity of the reporter protein will be measured using standard techniques known in the art. Transcription in the presence of protease can be compared with transcription in the absence of protease.

The invention also provides a method for screening compounds for inhibitory protease activity. A compound to be screened may be added at the same time the ligand is added or added during the initial expression/incubation of the protease with a fusion protein. The optimal level of compound needed to achieve the greatest inhibition of the protease may be determined by titration of the compound.

The invention also provides for a method for comparing the activity of two proteases which recognize the same protease cleavage site. The method is useful for comparing the activity of mutant and non-mutant proteases, e.g., HIV aspartyl proteases from patients.

The invention also provides a method for comparing the activity of a protease against different protease cleavage sites. This method is useful for determining substrate specificity of a given protease The invention also provides kits for assaying protease activity. If the kit is to be used in an in vitro transcription assay of a reporter gene, then it may comprise an in vitro transcription extract, a vector as described above containing a reporter gene, a supply of ligand, and instructions. Optionally, it may provide a supply of a fusion protein of this invention, a second protein comprising an expression modulator domain, and/or a protease expressed from a source including bacteria, insect cells, mammalian cells, and yeast.

If the kit is to be used in a cellular transcription assay, the kit may include a DNA sequence encoding a fusion protein of this invention and a vector encoding a reporter plasmid as described above, a ligand which associates with and regulates the activity of said fusion protein encoded by the DNA sequence of the protein; and instructions for using said kit to assay protease activity.

Proteases that are particularly useful in the methods of this invention are proteases that contribute to the symptoms or to the onset of a disease. For example, those proteases involved in digestion, blood clotting, apoptosis, activation of immune responses, zymogen activation, viral maturation, protein secretion and protein trafficking. In one embodiment of the invention, the proteases of interest are those involved in Alzheimer's disease, cystic fibrosis, emphysema, hypertension, tumor invasion and metastasis and viral-associated diseases. According to a preferred embodiment of this invention, the proteases are HIV aspartyl protease and HCV NS3 protease, and active fragments or fusion proteins thereof.

In one embodiment of this invention, any one or all of the DNA molecules encoding the fusion proteins, PBP's, proteases and second proteins comprising the expression modulator domain may be further modified to provide an additional polypeptide sequence for ease in purification or identifying of the expression of the protein. For example, such polypeptide sequences may include an epitope for binding an antibody, an Fc portion of an antibody for binding protein A beads, glutathione S transferase, maltose binding protein, His(n), FLAG, and Strep-tag. These screenable tags are all well known in the art and are fully available to the person skilled in the art.

Several vectors useful for overexpression of proteins of this invention are commercially available or known for expression in yeast, insect cells, bacteria, yeast, plant cells and mammalian cells.

Host cells useful according to the methods of this invention are well known in the art. If the activity of an exogenous protease is being studied, it is desirable that the host cell does not express high levels of endogenous proteases which recognize the protease cleavage site(s) being targetted. Suitable host cells may include CHO cells; HeLa cells; liver cells; CV-1 cells; P19 cells; NT2/D1 cells; mouse L cells; African Green monkey kidney cells, such as COS-7 cells or other COS cells; human embryonic kidney cells, such as HEK 293; DG44 cells, ltk- cells, mouse NIH 3T3 cells and yeast cells. The host cells may be transiently transfected or stably transformed cell lines. In a preferred embodiment of this invention, the host cells are COS cell or cells from a liver cell line.

Ligands suitable for use in the methods of this invention are well known in the art. The ligands should bind to the ligand binding domains of the transcription factors from which the ligand binding domains of the fusion proteins have been derived, or to modified ligand binding domains thereof (see above). Preferably, the ligand does not substantially enhance or repress transcription from the promoter unless a LRE for the fusion protein is spliced or inserted into an vector comprising a promoter and a reporter gene, wherein the LRE is linked to a promoter in a manner which makes transcriptional activity from the promoter operatively responsive to ligand.

Choice of ligand to use will necessarily depend on the ligand binding domain of the fusion protein being used. For example, suitable ligands for use with metal-binding DNA fusion proteins may include zinc, cadmium, and copper.

For example, suitable ligands for use with steroid binding or modified steroid binding fusion proteins may include androgen, glucocorticoid, mineralocorticoids, thyroid hormones, estrogen, progesterone, progestogen, retinoic acid, vitamin D3, 20-hydroxy-ecdysone, ponasterone A, 26-iodoponasterone A, muristerone A, inokosterone, 26-mesylinokosterone, mifepristone (RU 486) and analogs thereof.

As used herein, androgens include dihydroxytestosterone and analogs thereof including methyltrienolone.

As used herein, glucocorticoid hormones include cortisol, hydrocortisone, and corticosterone, and analogs therof including dexamethasone, deoxycorticosterone, and triamcinolone acetonide.

As used herein, mineralcorticoids include aldosterone, coricosterone and deoxycorticosterone.

As used herein, thyroid hormones include thyroxine (T4) and triodothyronine (T3).

As used herein estrogens include estradiol-17 beta, and analogs thereof indulcing diethylstilbestrol.

As used herein progestogens include analogs of progesterone including promegestrone.

Suitable ligands for tetracycline-inducible fusion protein include tetracycline and analogs thereof.

Suitable ligands for carbohydrate-inducible fusion proteins include arabinose, lactose, and isopropyl β-D-thiogalactoside (IPTG).

Suitable ligands for aryl hydrocarbon inducible fusion proteins include dioxin.

Suitable ligands for orphan receptors include the following: phytenic acid, 9-cis retinoic acid, and LG100268 for the RXR receptor; 8S-HETE and Wy 14,643 for the PPARα receptor; 15-deoxy-$\Delta^{12,14}$-PGJ2 and BRL 49653 for the PPARγ receptor; linoleic acid and carba-prostacyclin for the PPARδ receptor; farnesol for the FXR receptor; and 24(S), 25-epoxycholesterol for the LXR receptor. [B. M. Forman, (1998) "Orphan Nuclear Receptors and Their Ligands," *Molecular Biology of Steroid and Nuclear Hormone Receptors*, L. P. Freedman, Ed., Birhauser: Boston, pp. 281–305.]

The LREs and PBP-DNA elements in this invention are nucleic acid molecules that provide DNA binding sites for the fusion proteins and the protein binding partners, respectively. Both elements should be operatively linked to a promoter to control the activation or repression of transcription of a reporter gene. The phrase "operatively linked" refers to linking a nucleic acid molecule (e.g., a reporter gene encoding a reporter protein) to a LRE and a PBP-DNA element (if PBP binding is necessary for transcription) and to transcription control sequences in a manner such that the nucleic acid molecule molecule is able to be expressed when introduced (e.g., transfected, transformed, transduced, conjugated, or by recombination or by infection) into a host cell.

Transcription control sequences are sequences which control the initiation, elongation, and termination of transcription. Particularly important transcription control sequences are those which control transcription initiation such as the promoter. Preferably, the promoter is a minimal promoter. The term "minimal promoter" is intended to describe a partial promoter sequence which defines the start site of transcription for the linked sequence to be transcribed, but which by itself is not capable of initiating transcription efficiently, if at all, in a certain cell environment. Thus, the activity of such a minimal promoter is dependent upon the binding of a fusion protein of this invention.

In a preferred embodiment, the minimal promoter is from the drosophila heat shock promoter and the target LRE for the fusion protein is AGAACA generated as described in PCT/US97/05330 (incorporated by reference herein).

LREs according to this invention should be operative to confer responsiveness to a ligand. In a further embodiment, DNA elements that bind to PBP's of this invention may also be ligand-responsive if the PBP used is a ligand-binding protein. Choice of LRE and DNA element (as necessary) and the arrangement of those elements with respect to each other will depend upon the the fusion protein or the PBP used. For example, if the DNA-binding domain of the fusion protein is from a basic-helix-loop-helix protein, the LRE would likely comprise the consensus DNA hexamer CANNTG (also known as an "E box") (e.g., Littlewood, et al., supra, page 31).

The preferred DNA binding sites (i.e., LREs and DNA elements) for many transcription factors are known. [D. J. Mangelsdorf and R. M. Evans, (1992) "Retinoid Receptors as Transcription Factors," *Transcriptional Regulation*, Eds. S. L. McKnight and K. R. Yamamoto, pp. 1137–1167; L. P. Freedman, Ed., (1998) *Molecular Biology of Steroid and Nuclear Hormone Receptors: Progress in Gene Expression*, Birkhauser: Boston, Mass., pp. 111–113; and PCT/US97/05330 incorporated by reference herein.]

The promoter controlling the expression of the fusion proteins, PBP's, and proteases in a mammalian cell may be constitutive such as the cytomegalovirus (CMV) promoter, the SV40 early promoter, and the Rous Sarcoma Virus (RSV) promoter. For added control, the fusion protein, PBP's, and proteases may be under the control of an inducible promoter. It is desireable that the inducible promoter not be the same as the promoter that drives transcription of the reporter gene.

Reporter genes useful according to the methods of this invention are well known in the art. Such reporter genes include the luciferase gene, green fluorescent protein gene (U.S. Pat. No. 5,491,084), β-galactosidase, secreted alkaline phosphatase gene and the chloramphenicol acetyl transferase gene. Also, the invention contemplates reporter genes encoding a marker protein with a signal sequence for secretion out of the cell such as the IL-1 beta gene.

Vectors containing the reporter gene operatively linked to an LRE and DNA element (i.e., the reporter plasmid) may be prepared from materials available in the art. Such reporter plasmids preferably also include, for example, the following: an origin of replication and a selectable marker(s). The reporter plasmid may optionally also include other DNA sequences, such as long terminal repeats ("LTR's"), to cause the insertion of the vector into the genome of a cell line.

Vectors suitable for expressing the fusion proteins, PBP's, proteins having an expression modulator domain or proteases in bacteria or mammalian cells are well known in the art. Such vectors may for example include the following: an origin of replication, a selectable marker and transcription control sequences such as a promoter and a polyadenylation sequence. Thus, the fusion proteins, PBP's, proteins having expression modulator domains and proteases should be operatively linked to a constitutive or inducible promoter as described above. The vectors may be constructed such that two or more of the following proteins: the fusion protein, the protease, and optionally, the PBP and/or protein having the expression modulator domain (if necessary for fusion protein function) are present in the same vector. The transcription of these genes may be controlled by the same or different promoters. For example, each gene may be controlled by a different inducible promoter or each gene may be controlled by the same constitutive promoter.

The reporter plasmid and the vectors for expressing the fusion proteins, PBP's, proteases, and second proteins comprising the expression modulator domain may comprise two selectable markers—one that confers growth in prokaryotic cells such as bacteria and one that confers for growth in eukaryotic cells such as yeast, mammalian or plant cells in the presence of specific compounds. Selectable markers useful in this invention may confer resistance to drugs such as ampicillin, kanamycin, hygromycin, neomycin or G418.

In a preferred embodiment of this invention, the vector encodes the fusion protein (SEQ ID NO:20) having the DNA sequence SEQ ID NO:19. In a further preferred embodiment of this invention, a vector encoding the fusion protein (SEQ ID NO:22) having the DNA sequence, SEQ ID NO:21, is used as a control. In a preferred embodiment of this invention, the reporter plasmid is derived from pIND from Invitrogen.

If the vectors and reporter plasmids are to be: used in a transcriptional assay in a cell, they may be introduced into the host cells by techniques known in the art such as transfection, lipofectin, cytofectin, particle bead bombardment, electroporation, microinjection, or viral infection [e.g., F. M. Ausubel et al., Eds. *Current Protocols in Molecular Biology*, Greene Publishing Associates & Wiley-Interscience: New York (1991); Sambrook et al. *Molecular Clonina: A Laboratory Manual* 2nd. Ed., Cold Spring Harbor Laboratory Press (1989)].

In the case of viral infection, the DNA of interest may be cloned into a viral vector between two retroviral LTRs, used to generate retrovirus, and infect cells with the virus. Other viruses useful according to this invention include adenovirus, adeno-associated virus, and vaccinia virus.

Methods for assaying for the presence of a reporter gene product are well known in the art. For example, methods for assaying the mRNA resulting from the transcription of the reporter gene are known [Sambrook et al., (1989) *Molecular Cloning: A Laboratory Manual* (Cold Spring Harbor Lab. Press:Plainview, N.Y.), 2nd Ed.; Eds. F. M. Ausubel et al., (1991) *Current Protocols in Molecular Biology* (John Wiley & Sons: New York, 5th Ed.] Methods for assaying the protein encoded by the reporter gene are also known, and kits are available from companies for determining the same (e.g., Promega).

In order that the invention described herein may be more fully understood, the following examples are set forth. These examples are for illustrative purposes only and are not to be construed as limiting this invention in any manner.

EXAMPLE 1

Construction of DNA Vectors

A. Materials (1) Vectors

The plasmid pVgRXR was obtained from Invitrogen. pVgRXR is a 8728 kb vector that expresses both a modified Ecdysone Receptor (VgEcR) (SEQ ID NO:18) and a Retinoid X Receptor (RXR) to form a heterodimeric nuclear receptor (FIG. 1). Transcription of the VgEcR gene (SEQ ID NO:17) is driven by the cytomegalovirus (CMV) immediate early promoter. Transcription of the RXR gene is driven by the Rous sarcoma virus (RSV) promoter. Stable cell lines expressing the genes may be made by selection on the antibiotic Zeocin™. Product information regarding the features and the maintenance of the pVgRXR vector and the Ecdysone System kit are incorporated by reference from the Invitrogen technical manual.

Figure 3:
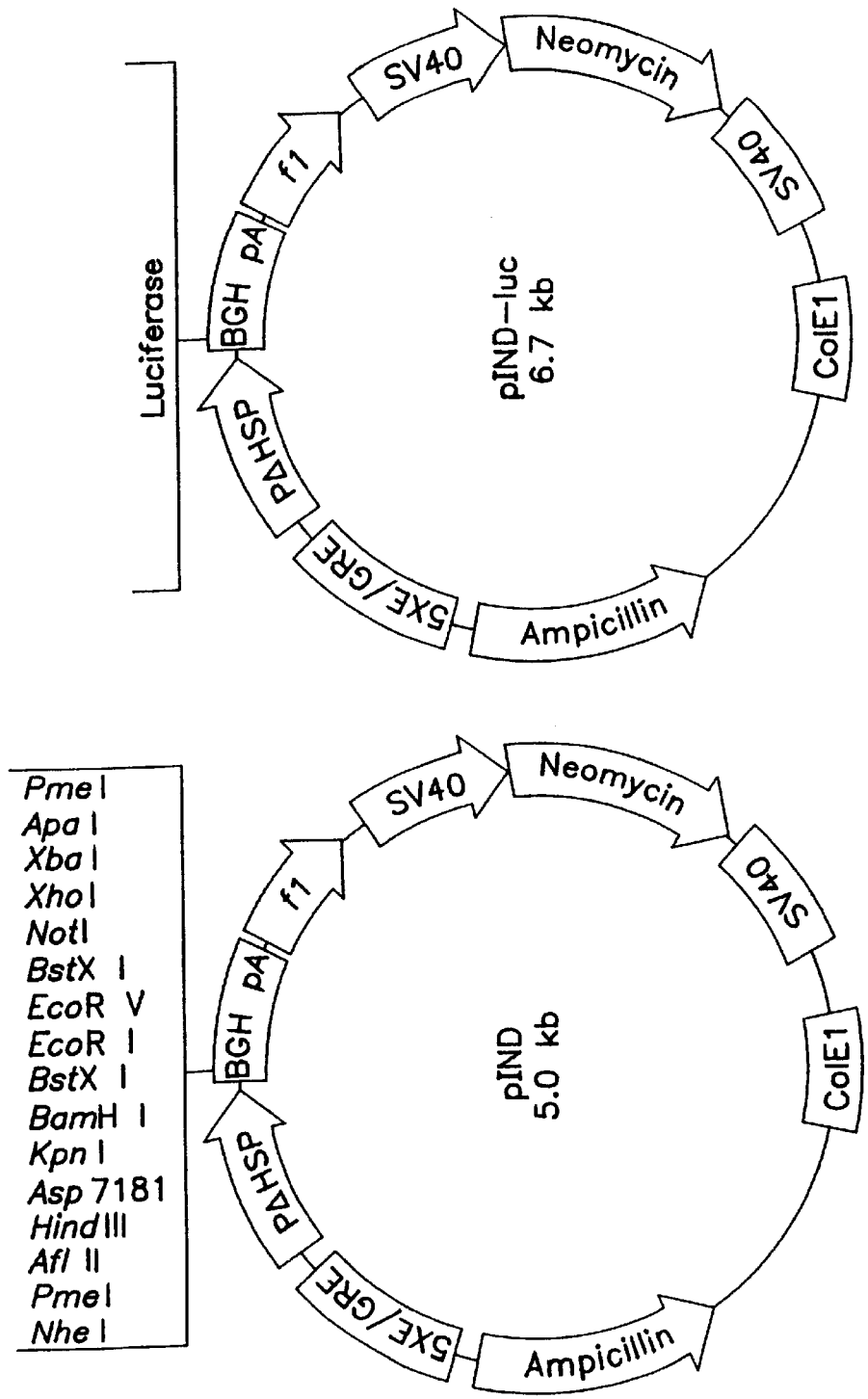
FIG. 3 depicts the structure of a control vector pIND and a reporter vector for Ecdysone-Inducible Luciferase Expression, pIND-luc.

The plasmids pIND was obtained from Invitrogen (FIG. 3). The plasmid pIND is a 5024 bp vector based on the pcDNA3.1 vector. It has five hybrid LREs, i.e., five ecdysone/glucocorticoid response elements (E/GRE), and the heat shock minimal promoter. The E/GRE's can be recognized by a modified ecdysone receptor expressed from pVgRXR. The plasmid pIND-Luc was made by digesting the luciferase gene out of another plasmid, including its Kozak sequence and methionine start site and cloning it into the poly linker of pIND, i.e., downstream of the minimal heat shock promoter (FIG. 3). Both plasmids have neomycin and ampicillin resistance genes for selection purposes. Product information regarding the features and the maintenance of the pIND and pIND-Luc vectors are incorporated by reference from the Invitrogen technical manual.

The mammalian expression plasmid pSRα has been described in the art [Y. Takebe et al., *Mol. Cell. Biol.*, 8, pp. 466–72 (1988) incorporated by reference herein]. The plasmid contains a promoter system composed of the simian virus 40 (SV40) early promoter and the R segment and part of the U5 sequence (R-U5') of the long terminal repeat of human T-cell leukemia virus type 1 (HTLV-1). The plasmid also contains a 16S splice junction, an SV40 polyadenylation signal and an ampicillin resistance gene. The HTLV LTR enhancer/promoter sequence drives high level expression of genes cloned downstream. Genes of interest may be cloned into the Pst I and EcoR1 cites located 3' to the 16S splice junction.

(2) Primers

The VP16/5A5BF primer (Seq. ID. No. 12) is a 28-mer designed to hybridize to an Xba I site upstream of the VP16 coding region of the pVgRXR plasmid.

The VP16/5A5BR primer (Seq. ID. No. 13) is a 86-mer designed to hybridize in part to the antisense strand in the 3' region of the DNA encoding the VP16 activation domain of the pVgRXR plasmid. The primer also comprises nucleotides complementary to the coding sequences for the 5A/5B cleavage site of the HCV NS3-4A protease and an Xba I site.

The VP16/5A**5BR primer (Seq. ID. No. 14) is a 92-mer designed to hybridize in part to the antisense strand in the 3' region of the DNA encoding the VP16 activation domain of the pVgRXR plasmid. The primer also has nucleotides sequences complementary to the coding sequences for the 5A/5B cleavage site of the HCV NS3-4A protease.

However, the DNA encoding the 5A/5B cleavage site additionally has a six nucleotide insertion between the DNA sequences encoding a cysteine and a serine codon. The six nucleotide insertion encodes two stop codons.

The NS3-4AF primer (Seq. ID. No. 15) is a 47-mer designed to bind partly to the start of the NS3 coding region (corresponding to amino acid #1027–1032 in the HCV polypeptide). The remainder of the oligonucleotide contains multiple restriction sites for ease of cloning.

The NS3-4AB primer (Seq. ID. No. 16) is a 44-mer designed to bind partly to the 3' end of the NS4A coding region (corresponding to amino acid #1705–1711 in the HCV polypeptide). The remainder of the oligonucleotide contains multiple restriction sites for ease of cloning.

Each primer was synthesized under standard conditions known in the art using an oligonucleotide synthesis machine.

B. Polymerase Chain Reactions (PCR) and Cloning Strategy

The PCR reactions were carried out under standard conditions (Sambrook, J., Fritsch, E. F., and Maniatis, T. (1989). *Molecular Cloning: A Laboratory Manual*. Second Edition., Plainview, N.Y.: Cold Spring Harbor Laboratory Press).

(1) pVgRXR-5A/5B vector and pVgRXR-5A**5A vector

The first step towards preparing the expression vector encoding VgRXR-5A/5B (Seq. ID. No. 19) involved a PCR reaction using the VP16/5A5BF primer (Seq. ID. No. 12), the VP16/5A5BR primer (Seq. ID. No. 13) and the pVgRXR plasmid as the template. Next, the PCR product was digested with Xba I. A vector for ligation with the PCR product was prepared by digesting the pVgRXR vector with Xba I to remove the DNA encoding the VP16 activation domain. The vector backbone was isolated and the digested, PCR insert was ligated into the Xba I site in the backbone. The ligations were screened by sequencing to ensure the proper orientation of the insert and correctness of its nucleotide sequence.

The first step towards preparing the expression vector encoding VgRXR-5A5B (Seq. ID. No. 21) involved a PCR reaction using the VP16/5A5BF primer (Seq. ID. No. 12), the VP16/5A5BR primer (Seq. ID. No. 14) and the pVgRXR plasmid as the template. Next, the PCR product was digested with Xba I. A vector for ligating with the PCR product was prepared by digesting the pVgRXR vector with Xba I to remove the DNA encoding the VP16 activation domain. The vector backbone was isolated and the digested PCR insert was ligated into the Xba I site in the backbone. The ligations were screened by sequencing to ensure the proper orientation of the insert and the correctness of its nucleotide sequence.

(2) pSRα-NS3-4A and pSRα-NS3-4A(S1165A)

The first step towards preparing the pSRα-NS3-4A vector encoding the NS3-4A cleavage site (Seq. ID. No. 10) involved a PCR reaction using the NS3-4AF primer (Seq. ID. No. 15), the NS3-4AB primer (Seq. ID. No. 16) and full length HCV H strain cDNA as a template [Inchauspe et al., (1991), PNAS USA 88:10292–10296 incorporated by reference herein]. Next, the PCR product was digested with Pst1 and EcoR1. A vector for ligating with the PCR product was prepared by digesting the pSRα vector with Pst 1 and EcoR1. The vector backbone was isolated and the PCR insert was ligated into the Pst1-EcoR1 site in the backbone.

The first step towards preparing the pSRα-NS3-4A (S1165A) vector encoding the NS3-4A mutant protease involved a PCR reaction using the NS3-4AF primer (Seq. ID. No. 15), the NS3-4AB primer (Seq. ID. No. 16) and the cDNA of the NS3 active site mutant S1165A [A. Grakoui et al., (1993) *J. Virology* 67: 2832–43 incorporated by reference herein]. Next, the PCR product was digested with Pst1 and EcoR1. A vector for ligating with the PCR product was prepared by digesting the pSRα vector with Pst1 and EcoR1. The vector backbone was isolated and the PCR insert was ligated into the Pst1-EcoR1 site in the backbone. The NS3-4A(S1165A) has a serine to alanine substitution at amino acid number 1165, which makes the protease inactive. Compare Seq ID Nos. 10 and Seq ID No. 11.

EXAMPLE 2

The NS3-4A Protease Ecdysone-Inducible Luciferase Assay

HCV NS3-4A protease ecdysone-inducible luciferase assays were generally carried out as described below.

COS African green monkey kidney cells were plated at approximately 150,000 cells/well in a 6-well plate. The next day, approximately 3.6 $\mu$g plasmid DNA was dissolved in 100 $\mu$l of Dulbecco's modified Eagle's media-Gibco BRL (DMEM), combined with 29 $\mu$l of Superfect reagent (Qiagen), and then mixed by pipetting. The mixture was incubated at room temperature for ten minutes.

The amounts of DNA typically used in each experiment was as follows: 0.6 $\mu$g of pIND-Luc, 0.6 $\mu$g of pVgRXR-5A/5B or pVgRXR-5A**5B, and 0–2.4 $\mu$g of pSRα-NS3-4A or pSRα-NS3-4A(S1165A) or pSRα.

Next 600 $\mu$l of DMEM with v/v 10% fetal bovine serum (10% FBS-DMEM) was added to the DNA mixture and mixed by pipetting. The cells in the 6-well plate were washed with 2.5 ml phosphate-buffered saline (PBS). The PBS was removed from the cells and replaced by the DNA mixture. The cells were incubated in the DNA mixture for three hours at 37° C. in a 5% $CO_2$ incubator.

After incubation, the cells were washed with PBS. The PBS was removed and 10% FBS-DMEM was added to the cells. The cells were incubated in 10% FBS-DMEM overnight at 37° C. in a 5% $CO_2$ incubator.

On the next day, an exogenous ligand was added to the cells to induce transcription of the reporter gene. Specifically, the 10% FBS-DMEM was aspirated off the cells and replaced with a 10% FBS-DMEM solution containing a concentration of 1–10 $\mu$M muristerone A or 1–10 $\mu$M ponasterone A (Invitrogen, United Kingdom). In some cases, a protease inhibitor dissolved in dimethylsulfoxide (DMSO) was also added to the cells for a final concentration of 1–40 $\mu$M. The cells were incubated with muristerone A or ponasterone A for 24 hours at 37° C. in a 5% $CO_2$ incubator.

The following day, the cells were washed with PBS. The activity of the luciferase protein was measured using a luciferase assay kit (Promega). Specifically, the cells were lysed in 250 $\mu$l of Cell Culture Lysis Reagent. The cells were scraped from the plate and transferred to a microfuge tube. The extract was spun at 12,000×g for 5 seconds. Twenty microliters of each sample was added to 100 $\mu$l of Luciferase Assay Reagent. The light produced by the reaction of the luciferase with the Reagent was measured in a luminometer and was reported as relative light units (RLU).

Most of the experiments were done several times in triplicate. Error bars reflecting the standard deviation of the data points are included in the Figures.

EXAMPLE 3

Figure 4:
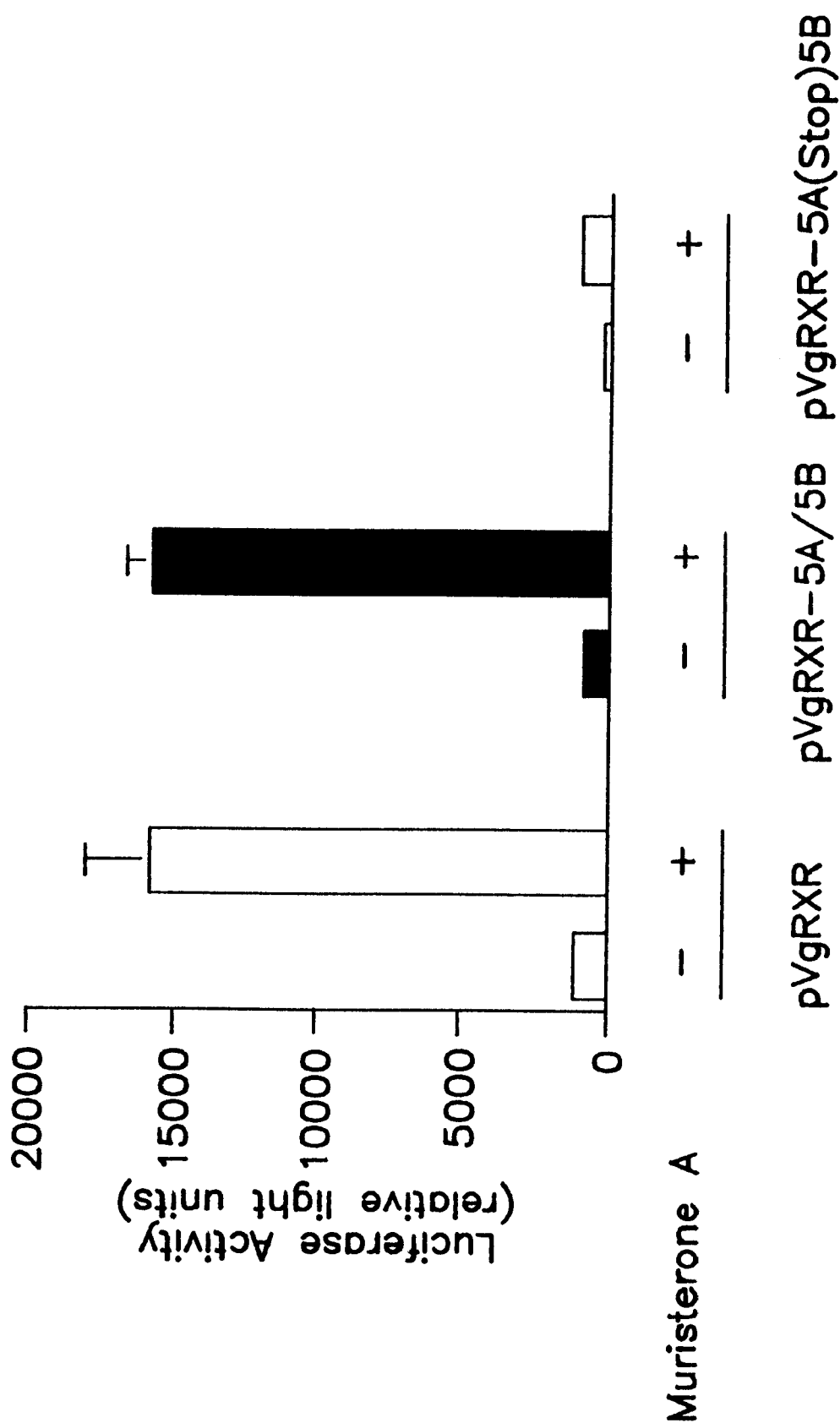
FIG. 4 graphically depicts the results of transfections experiments into COS cells with any one of the following: (1) a DNA vector encoding a mammalian RXR receptor protein and a fusion protein comprising the DNA-binding domain of the Drosophila ecdysone receptor fused to the activation domain of the Herpes simplex virus VP16 protein (pVgRXR); (2) a DNA vector encoding an RXR receptor protein and a fusion protein comprising the DNA-binding domain of the Drosophila ecdysone receptor fused to the 5A/5B proteolytic cleavage site of HCV fused to the activation domain of the VP16 protein (pVgRXR-5A/5B); and (3) a DNA vector encoding a RXR receptor protein and a fusion protein as described above except that the DNA encoding the 5A/5B cleavage site is modified to contain tandem stop codons in the cleavage site (pVgRXR-5A(Stop) 5B). A plasmid comprising a luciferase reporter gene was included in each transfection (pIND-luc). After the transfection, transcription of the reporter gene was induced by administering 1 $\mu$M muristerone A (an ecdysone analog) to the transfected cells. The data was obtained by measuring the luciferase activity present in the lysates from the transfected cells as described in Example 2.

The Insertion of a 5A/5B Junction between the Activation Domain and the DNA-binding Domain Does Not Interfere with Muristerone A-Induced Transactivation Vectors encoding fusion proteins (VgRXR, VgRXR-5A/5B, or VgRXR-5A(Stop)5B) and pIND-Luc were transfected into COS cells as described above (Example 2). On the following day, some of the cells were incubated with 1 µM of muristerone for 24 hours. The cells were lysed and assayed for luciferase activity as described previously. The results are depicted in FIG. 4.

The control fusion protein expressed by pVgRXR-5A (Stop)5B, which lacks the ecdysone DNA binding domain shows negligible activity. Little or no difference is observed between the activities of the VgRXR and the VgRXR-5A/5B expressed fusion proteins. The results indicate that the insertion of the 5A/5B junction in the VgRXR expressed protein does not interfere with muristerone A-induced activity.

EXAMPLE 4

Figure 5:
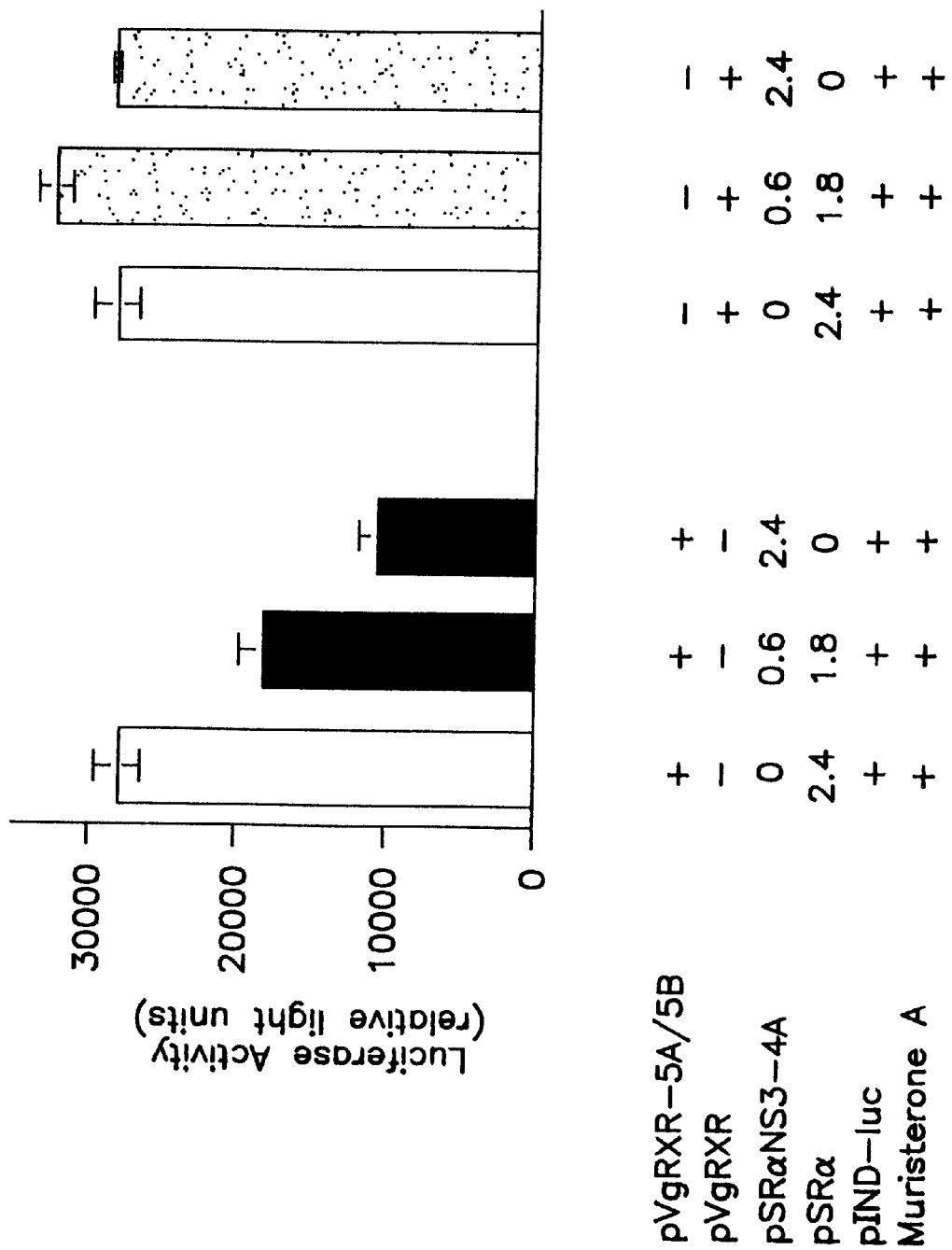
FIG. 5 depicts the results of cotransfecting plasmids pVgRXR-5A/5B and pIND-luc into COS cells with increasing amounts of a plasmid encoding HCV NS3-4A protease (pSRαNs3-4A) or of a control plasmid (pSRα). After the transfection, transcription of the reporter plasmid was induced by administering 1 $\mu$M muristerone A to the transfected cells.

Cotransfection of Increasing Amounts of pSRαNS3-4A With pVgRXR-5A/5B Leads to a Dose-Dependent Decrease of Muristerone A-Inducible Transactivation The reporter plasmid pIND-Luc was cotransfected with either pVgRXR-5A/5B or pVgRXR and increasing amounts (µgs) of the DNA encoding the protease NS3-4A as indicated in FIG. 5. On the following day, the cells were incubated in 1 µM muristerone A. Next, the cells were lysed and assayed for luciferase activity as described previously. The results are depicted in FIG. 5.

Transcription of the luciferase reporter construct when co-transfected with the VgRXR construct encoding mammalian RXR and the ecdysone receptor/VP16 fusion proteins showed little or no change when coexpressed with the protease NS3-4A. The VgRXR-5A/5B encoded protein, on the other hand, produced a dosage-dependent decrease in luciferase activity when coexpressed with the NS3-4A protein. These results suggest that the protease NS3-4A cleaves the 5A/5B junction but not other areas of the fusion protein necessary for activity.

EXAMPLE 5

Figure 6:
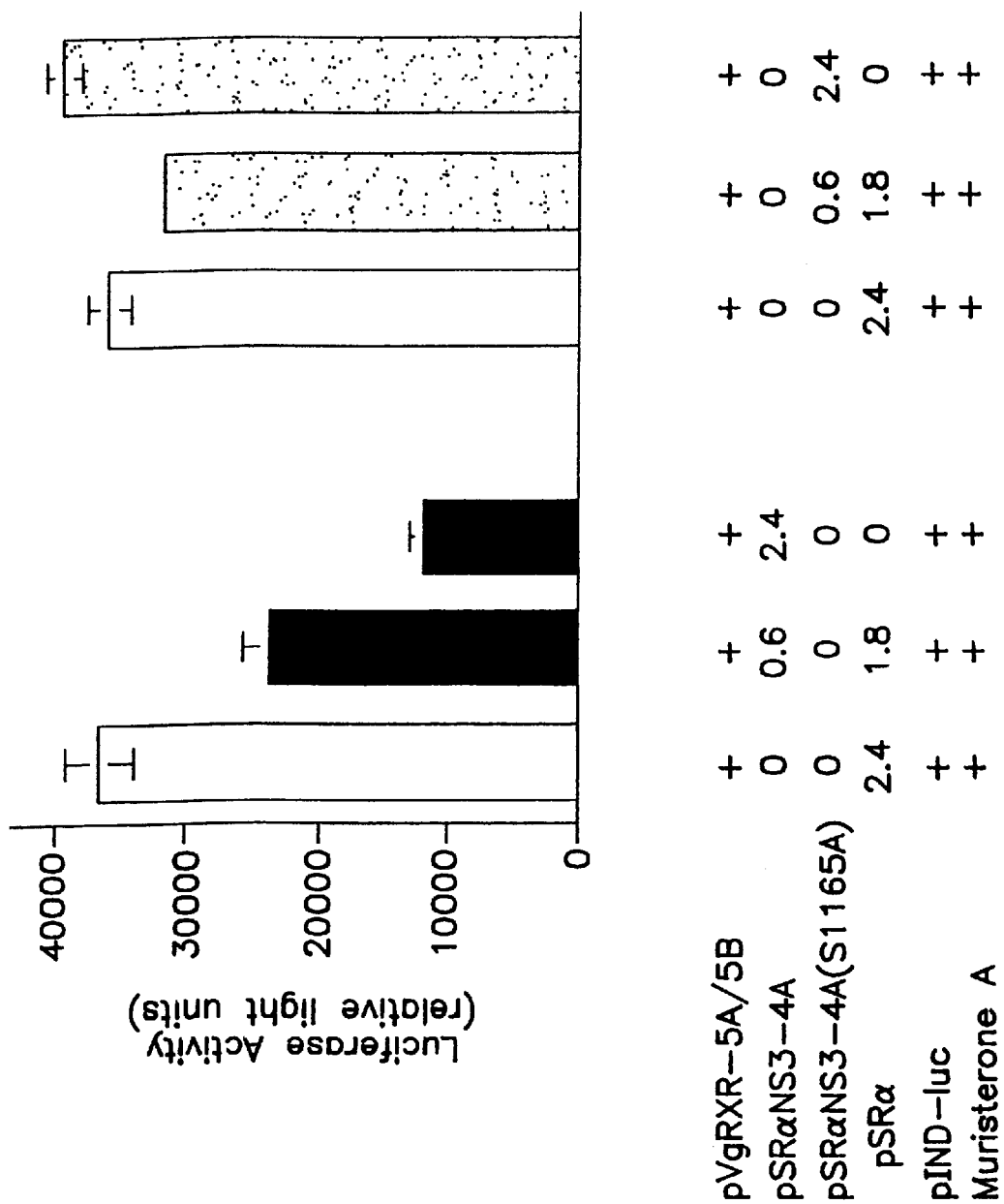
FIG. 6 graphically depicts the results of cotransfecting plasmids pVgRXR-5A/5B and pIND-luc into COS cells with increasing amounts of a plasmid encoding HCV NS3-4A protease or an inactivate mutant thereof (pSRαNs3-4A or pSRαNs3-4A(S1165A), respectively). After the transfection, transcription of the reporter gene was induced by administering 1 $\mu$M muristerone A to the transfected cells.

Cotransfection of Increasing Amounts of pSRαNS3-4A(S1165A) with pVgRXR-5A/5B Does Not Affect Muristerone A-Inducible Transactivation We used 0.6 µgs of pVgRXR-5A/5B and 0.6 µgs of pIND-Luc to cotransfect with varying amounts (µgs) of the vectors encoding NS3 protease or an inactive mutant thereof as indicated in FIG. 6. The total amount of DNA used for each transfection was 3.6 µgs with the addition of pSRα. On the following day, the cells were incubated in 1 µM of muristerone A. The cells were lysed and assayed for luciferase activity as described previously. The results are depicted in FIG. 6.

As seen in the previous results (Example 4), the fusion protein encoded by VgRXR-5A/5B demonstrated a high level of activity in the absence of the NS3-4A protease. The activity of VgRXR-5A/5B-mediated luciferase activity decreased in a dosage-dependent manner with the cotransfection of DNA encoding the NS3-4A protease, but not with the DNA encoding the mutant protease NS3-4A(S1165A). This is presumably due to the inability of the mutant NS3-4A protease to cleave the ecdysone/VP16 fusion protein.

Dosage-dependence studies such Examples 4 and 5 were useful for determining the optimal ratio of DNA encoding fusion protein and DNA encoding protease for use in future assays.

EXAMPLE 6

Ponasterone A Dose Response

Figure 7:
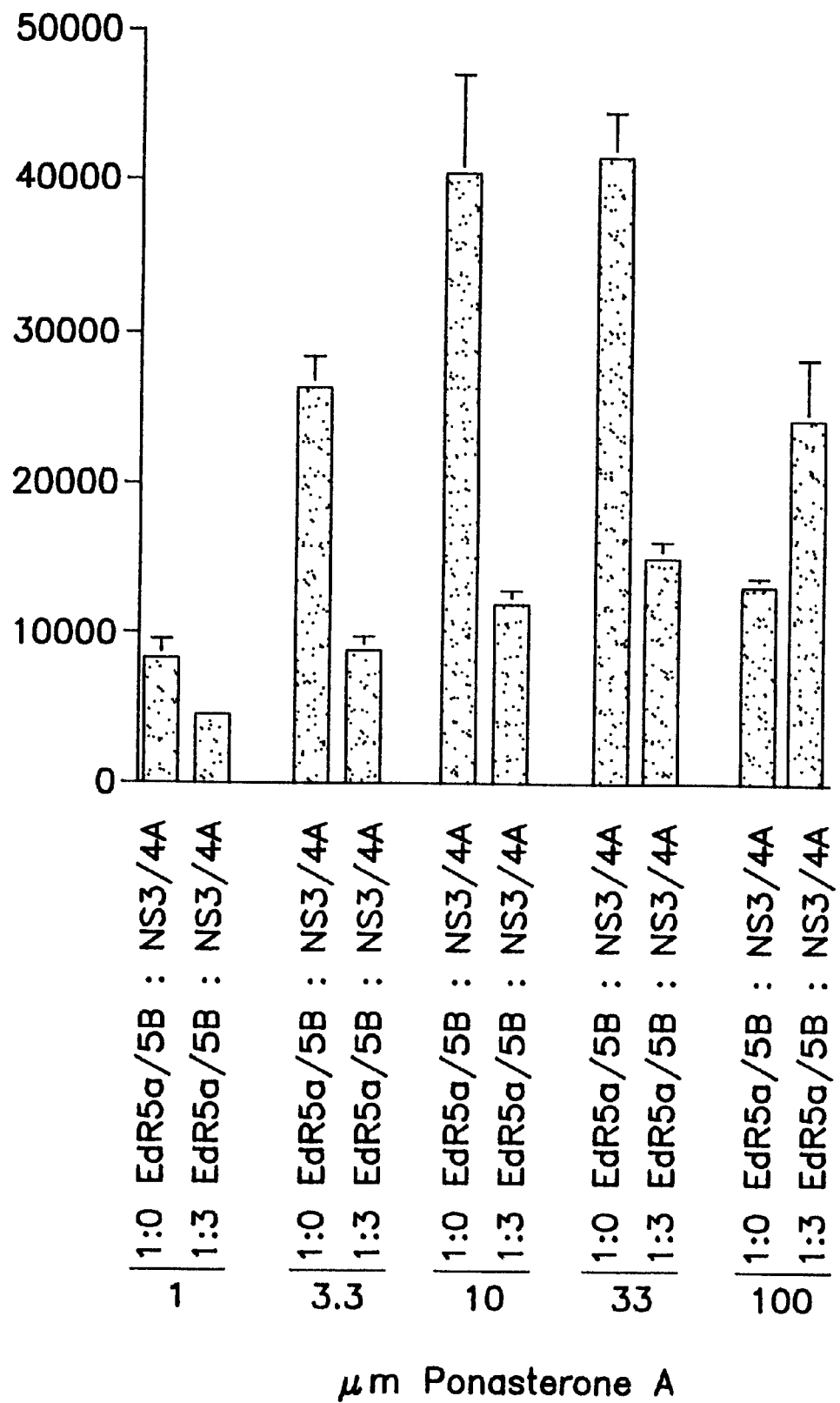
FIG. 7 graphically depicts the results of administering either 1, 3.3, 10, 33 or 100 $\mu$M of ponasterone A (an ecdysone analog) to COS cells after cotransfection with plasmids pVgRXR-5A/5B and pIND-Luc in the presence or absence of a plasmid encoding the HCV-NS3-4A protease (pSRαNs3-4A).

The plasmid pIND-Luc (0.6 µg) was cotransfected with pVgRXR-5A/5B (0.6 µg) in the absence or presence of 1.8 µg of pSRαNS3-4A. On the following day, the cells were incubated with varying amounts of ponasterone A, a ligand which induces the neterodimerization of ecdysone receptor with the mammalian retinoic acid receptor, RXR. The cells were lysed and assayed for luciferase activity as described previously. The results are depicted in FIG. 7.

The results indicate that ponasterone A is effective at activating the fusion protein EdR5A/5B (i.e., the protein encoded by VgRXR-5A/5B) in the absence of the protease NS3-4A. For the purposes of these experiments, the greatest activation of the fusion protein occurred when ponasterone A was present in a concentration between 3.3–10 µM. Generally, ponasterone A was found to be equally effective at inducing transcription as muristerone A in these assays.

EXAMPLE 7

Ponasterone A Induction and % DMSO Control

Figure 8:
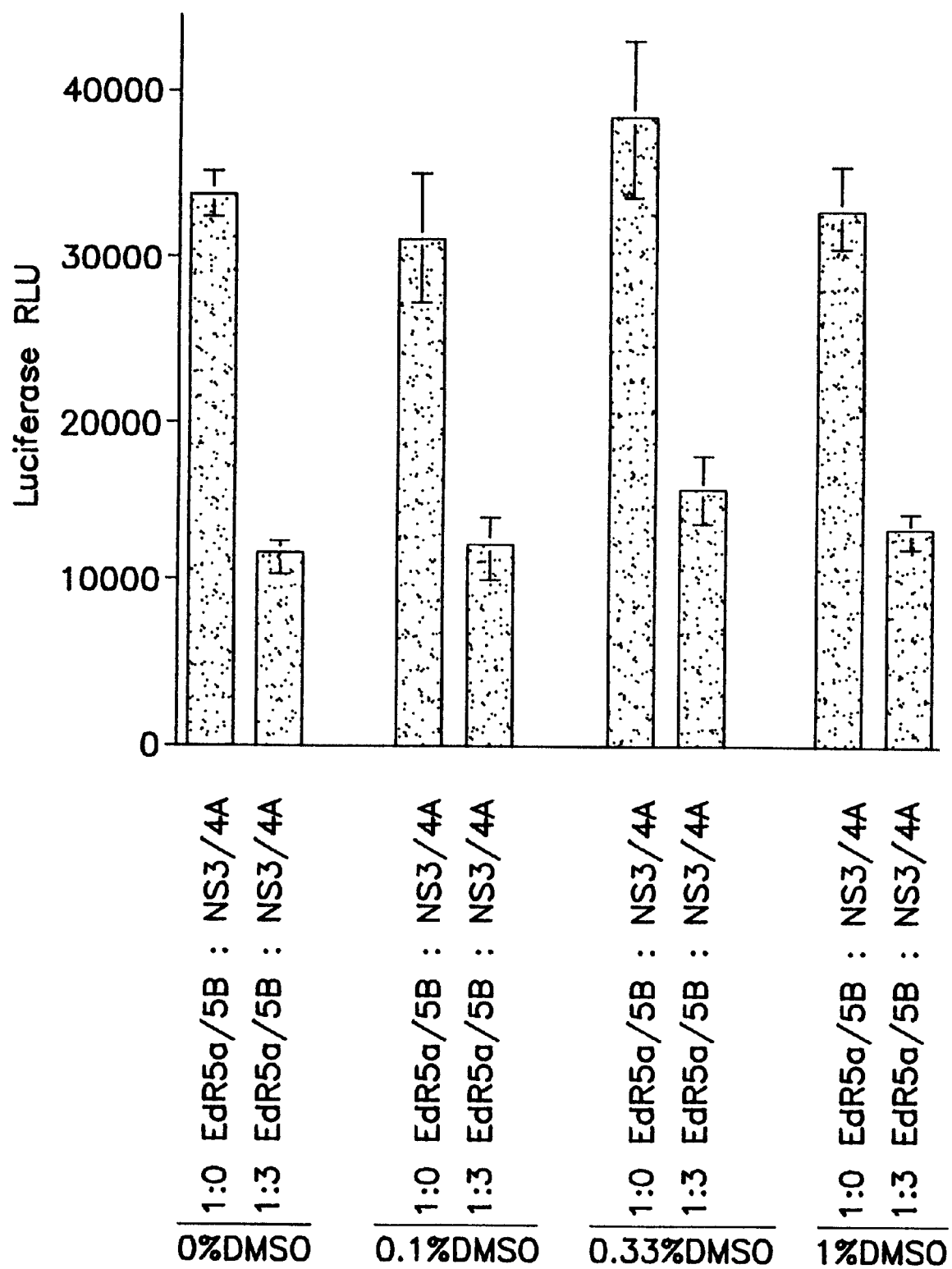
FIG. 8 graphically depicts the results of a control experiment demonstrating DMSO tolerance. Plasmids pVgRXR-5A/5B and pIND-Luc were cotransfected into COS cells with or without a plasmid encoding the HCV-NS3-4A protease (pSRαNs3-4A). After the transfection, transcription of the reporter plasmid was induced by administering 5 $\mu$M ponasterone A in the presence of increasing concentrations of dimethylsulfoxide (DMSO).

The plasmid pIND-Luc (0.6 µg) was cotransfected with pVgRXR-5A/5B (0.6 µg) in the absence or presence of 1.8 µg of pSRαNS3-4A. On the following day, the cells were incubated with 5 µM ponasterone A. Dimethylsulfoxide (DMSO) was also added to the cells to a final concentration of 0–1% DMSO (v/v). The cells were lysed and assayed for luciferase activity as described previously. The results are depicted in FIG. 8.

In this control experiment, DMSO was added to cells to determine whether the presence of it interfered with the activation of the fusion protein by ponasterone A. DMSO is a solvent that was sometimes used to dissolve protease inhibitor compounds prior to addition to these assays. In most experiments, the DMSO concentration in cell culture did not exceed 0.1%. The results indicate that DMSO concentrations up to 1% had little or no effect on the ponasterone A-induced luciferase activity in this assay.

The Examples below demonstrate how this assay may be useful to screen compounds potentially useful as inhibitors of a protease.

EXAMPLE 8

Dose Dependent Inhibition of NS3-4A Activity by VH-25,531

Figure 9:
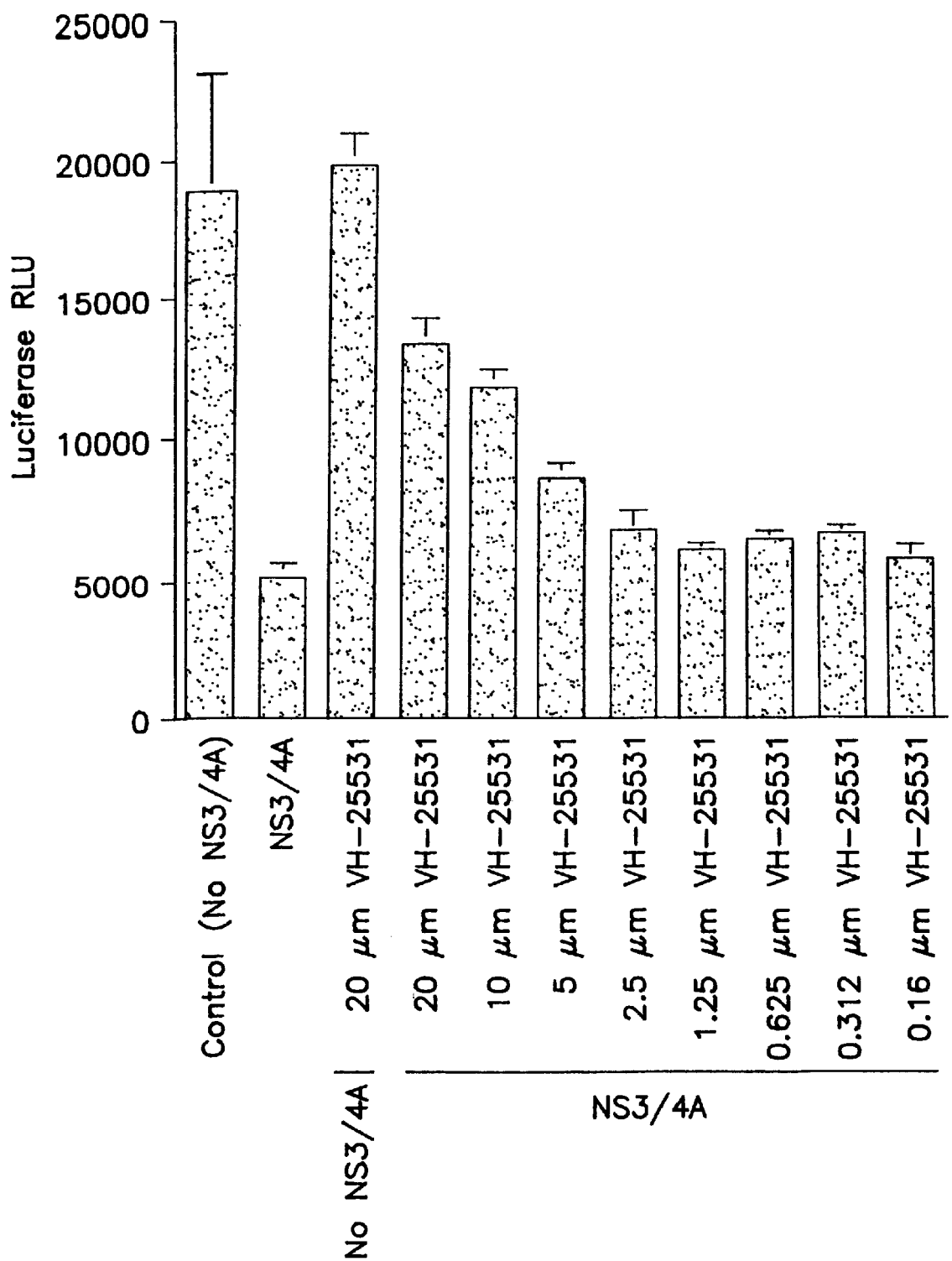
FIG. 9 graphically depicts the results of cotransfecting plasmids pVgRXR-5A/5B, pIND-Luc and pSRαNS3-4A into COS cells and then administering 5 $\mu$M ponasterone A and varying amounts of a protease inhibitor (VH-25531).

The plasmid pIND-Luc (0.6 µg) was cotransfected with pVgRXR-5A/5B (0.6 µg) in the presence of 1.8 µg of pSRαNS3-4A (1:3 ratio). On the following day, the cells were incubated with 5 µM ponasterone A and varying amounts of a compound VH-25531 as indicated in FIG. 9. The cells were lysed and assayed for luciferase activity as described previously. The results are depicted in FIG. 9.

The results indicate that VH-25531 in the absence of the NS3-4A protease does not significantly increase or decrease the activity of the fusion protein (compare lanes 1 and 3, FIG. 9). However, VH-25531 does inhibit the activity of the NS3-4A protease especially at 20 µM (compare lanes 4–11 with claim 2, FIG. 9). In fact, the results indicate that VH-25531 may inhibit the NS3-4A protease as much as 55.5% at a 20 µM concentration. The percent inhibition of protease activity at 20 µM VH-25531 was roughly calculated by subtracting the values of lanes 3 and 2 (19900–5177=14732), by subtracting the values of lanes 4 and 2 (13356–5177=8179), and then by dividing the two values (8179/14723=0.555).

While we have hereinbefore presented a number of embodiments of this invention, it is apparent that our basic construction can be altered to provide other embodiments which utilize the methods of this invention. Therefore, it will be appreciated that the scope of this invention is to be defined by the claims and specification rather than the specific embodiments which are exemplified here.

We claim:

1. A method for assaying protease activity in a cell comprising the steps of:
   a. culturing a host cell comprising:
      (1) a DNA molecule encoding a fusion protein comprising:
         (i) a protease cleavage site;
         (ii) a ligand binding domain; and
         (iii) a DNA binding domain;
      wherein the association of a ligand with said fusion protein mediates the binding of the fusion protein to a ligand-responsive element ("LRE") operatively linked to a reporter gene wherein said protease cleavage site of said fusion protein can be cleaved such that neither of the resulting fusion protein fragments are capable of modulating the expression of said reporter gene and wherein the fusion protein also comprises an expression modulator domain or associates with a second protein having an expression modulator domain, wherein said expression modulator domain regulates the transcription of said reporter gene; and
      (2) a DNA molecule comprising:
         (i) an LRE that binds to said DNA binding domain of said fusion protein, wherein said binding is modulated by the presence of a ligand and is optionally modulated by the presence of a protein binding partner of said fusion protein;
         (ii) a promoter that is modulated by the expression modulator domain of the fusion protein or the second protein; and
         (iii) a reporter gene, the expression of which is controlled by said promoter;
   b. adding to said host cell culture a ligand that associates with and regulates the activity of said fusion protein, wherein said ligand is required for said fusion protein to (i) bind to said LRE or to bind to a protein binding partner; and (ii) regulate the transcription of said reporter gene via the expression modulator domain of the fusion protein or the second protein; and
   c. quantifying a gene product produced from said reporter gene.

2. A method of comparing the activity of two proteases that recognize the same cleavage site, said method comprising the steps of:
   a. culturing a first host cell comprising:
      (1) a DNA molecule encoding a fusion protein comprising:
         (i) a protease cleavage site;
         (ii) a ligand binding domain; and
         (iii) a DNA binding domain;
      wherein the association of a ligand with said fusion protein mediates the binding of the fusion protein to a ligand-responsive element ("LRE") operatively linked to a reporter gene; wherein said protease cleavage site of said fusion protein can be cleaved such that neither of the resulting fusion protein fragments are capable of modulating the expression of said reporter gene and wherein the fusion protein also comprises an expression modulator domain or associates with a second protein having an expression modulator domain, wherein said expression modulator domain regulates the transcription of said reporter gene; and (2) a DNA molecule comprising:
  (i) an LRE that binds to said DNA binding domain of said fusion protein, wherein said binding is modulated by the presence of a ligand and is optionally modulated by the presence of a protein binding partner of said fusion protein;
  (ii) a promoter that is modulated by the expression modulator domain of the fusion protein or the second protein; and
  (iii) a reporter gene, the expression of which is controlled by said promoter;
b. culturing a second host cell comprising the DNA molecules of (1) and (2) wherein said protease cleavage site of said fusion protein can be cleaved such that neither of the resulting fusion protein fragments are capable of modulating the expression of said reporter gene;
c. adding to said first and to said second host cell culture a ligand, wherein said ligand is required for said fusion proteins in said first and second host cells to (i) bind to said LRE operatively linked to a reporter gene or to bind to a protein binding partner; and (ii) modulate the transcription of said reporter gene via the expression modulator domain of the fusion protein or the second protein; and
d. comparing the amount of gene product produced from said reporter gene in said first host cell culture and said second host cell culture.

3. The method according to claim 1 or claim 2, wherein said protease cleavage site of the fusion protein is recognized by HCV NS3 protease.

4. The method according to claim 1 or claim 2, wherein said protease cleavage site of the said fusion protein is recognized by HIV aspartyl protease.

5. The method according to claim 1 or claim 2, wherein said DNA binding domain of said fusion protein is selected from a DNA binding domain of a steroid/thyroid superfamily receptor.

6. The method according to claim 1 or claim 2, wherein said DNA binding domain of said fusion protein is from the ecdysone receptor and wherein said ecdysone receptor requires association with a protein binding partner to enable binding to DNA.

7. The method according to claim 6, wherein said DNA binding domain of said fusion protein is modified such that the P-box region has the amino acid sequence SEQ ID NO:24.

8. The method according to claim 1 or claim 2, wherein said expression modulator domain of said fusion protein is the activation domain of the VP16 protein.

9. The method according to claim 1 or claim 2 wherein the fusion protein has an amino acid sequence comprising the sequence of SEQ ID NO:20 or SEQ ID NO:22.

10. The method according to claim 1 or claim 2, wherein the amino acid sequence of the protease cleavage site is selected from the group consisting of SEQ ID NOs:1–10.

11. The method according to claim 1 or claim 2 wherein the DNA molecule encoding said fusion protein comprises the sequence of SEQ ID NO:19 or SEQ ID NO:21.

12. The method according to claim 1 or claim 2, wherein a vector encodes said fusion-protein.

13. The method according to claim 1 or claim 2, wherein said promoter is a mammalian heat shock promoter.

14. The method according to claim 1 or claim 2, wherein said reporter gene is the luciferase gene.

15. The method according to claim 1 or claim 2, additionally comprising a DNA molecule which encodes a protein binding partner necessary for activating said DNA binding domain of said fusion protein.

* * * * *

```
                          SEQUENCE LISTING

<160> NUMBER OF SEQ ID NOS: 24

<210> SEQ ID NO 1
<211> LENGTH: 10
<212> TYPE: PRT
<213> ORGANISM: Human immunodeficiency virus

<400> SEQUENCE: 1

Val Ser Phe Asn Phe Pro Gln Ile Thr Leu
 1               5                  10

<210> SEQ ID NO 2
<211> LENGTH: 8
<212> TYPE: PRT
<213> ORGANISM: Human immunodeficiency virus

<400> SEQUENCE: 2

Ser Gln Asn Tyr Pro Ile Val Gln
 1               5

<210> SEQ ID NO 3
<211> LENGTH: 8
<212> TYPE: PRT
<213> ORGANISM: Human immunodeficiency virus

<400> SEQUENCE: 3

Ala Arg Val Leu Ala Glu Ala Met
 1               5

<210> SEQ ID NO 4
<211> LENGTH: 8
<212> TYPE: PRT
<213> ORGANISM: Human immunodeficiency virus

<400> SEQUENCE: 4

Ala Asn Ile Met Met Gln Arg Gly
 1               5

<210> SEQ ID NO 5
<211> LENGTH: 8
<212> TYPE: PRT
<213> ORGANISM: Human immunodeficiency virus

<400> SEQUENCE: 5

Pro Gly Asn Phe Leu Gln Ser Arg
 1               5

<210> SEQ ID NO 6
<211> LENGTH: 8
<212> TYPE: PRT
<213> ORGANISM: Human immunodeficiency virus

<400> SEQUENCE: 6

Ser Phe Asn Phe Pro Gln Ile Thr
 1               5

<210> SEQ ID NO 7
<211> LENGTH: 8
<212> TYPE: PRT
<213> ORGANISM: Human immunodeficiency virus
```

<400> SEQUENCE: 7

Gln Ile Thr Leu Trp Gln Arg Pro
 1               5

<210> SEQ ID NO 8
<211> LENGTH: 8
<212> TYPE: PRT
<213> ORGANISM: Human immunodeficiency virus

<400> SEQUENCE: 8

Thr Leu Asn Phe Pro Ile Ser Pro
 1               5

<210> SEQ ID NO 9
<211> LENGTH: 8
<212> TYPE: PRT
<213> ORGANISM: Human immunodeficiency virus

<400> SEQUENCE: 9

Arg Lys Val Leu Phe Leu Asn Gly
 1               5

<210> SEQ ID NO 10
<211> LENGTH: 18
<212> TYPE: PRT
<213> ORGANISM: Hepatitis C virus

<400> SEQUENCE: 10

Gly Ala Asp Thr Glu Asp Val Val Cys Cys Ser Met Ser Tyr Thr Trp
 1               5                  10                  15

Thr Gly

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:mutated
      hepatitis C virus

<400> SEQUENCE: 11

Gly Ala Ala Thr Glu Asp Val Val Cys Cys
 1               5                  10

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:man-made
      artificial sequence

<400> SEQUENCE: 12
agctagctct agagtaccga gctcggat                                          28

<210> SEQ ID NO 13
<211> LENGTH: 86
<212> TYPE: DNA
<213> ORGANISM: Artificial Sequence
<220> FEATURE:
<223> OTHER INFORMATION: Description of Artificial Sequence:man-made
      artificial sequence

<400> SEQUENCE: 13

-continued

| tcgtctagag cctgtccagg tataagacat tgagcagcac acgacatctt ccgtgtcggc | 60 |
| gccggtacct agaagcttcc caccgt | 86 |

<210> SEQ ID NO 14
<211> LENGTH: 92
<212> TYPE: DNA
<213> ORGANISM: Artificial Sequence
<220> FEATURE:
<223> OTHER INFORMATION: Description of Artificial Sequence:man-made
      artificial sequence

<400> SEQUENCE: 14

| tcgtctagag cctgtccagg tataagacat tgatcatcag cagcacacga catcttccgt | 60 |
| gtcggcgccg gtacctagaa gcttcccacc gt | 92 |

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence:man-made
      artificial sequence

<400> SEQUENCE: 15

| ggactagtct gcagtctaga gctccatggc gcccatcacg gcgtacg | 47 |

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence:man-made
      artificial sequence

<400> SEQUENCE: 16

| gaagatctga attctagatt ttagcactct tccatctcat cgaa | 44 |

<210> SEQ ID NO 17
<211> LENGTH: 2241
<212> TYPE: DNA
<213> ORGANISM: Artificial Sequence
<220> FEATURE:
<223> OTHER INFORMATION: Description of Artificial Sequence:man-made
      artificial sequence

<400> SEQUENCE: 17

| atggccccc cgaccgatgt cagcctgggg gacgaactcc acttagacgg cgaggacgtg | 60 |
| gcgatggcgc atgccgacgc gctagacgat ttcgatctgg acatgttggg ggacggggat | 120 |
| tccccaggtc cgggatttac cccccacgac tccgcccccct acggcgctct ggatatggcc | 180 |
| gacttcgagt ttgagcagat gtttaccgat gcccttggaa ttgacgagta cggtgggaag | 240 |
| cttctaggta cctctagaag aatatcaaat tctatatctt caggtcgcga tgatctctcg | 300 |
| ccttcgagca gcttgaacgg atactcggcg aacgaaagct gcgatgcgaa gaagagcaag | 360 |
| aagggacctg cgccacgggt gcaagaggag ctgtgcctgg tttgcggcga cagggcctcc | 420 |
| ggctaccact acaacgccct cacctgtggg gctgcaagg ggttctttcg acgcagcgtt | 480 |
| acgaagagcg ccgtctactg ctgcaagttc gggcgcgcct gcgaaatgga catgtacatg | 540 |
| aggcgaaagt gtcaggagtg ccgcctgaaa aagtgcctgg ccgtgggtat gcggccggaa | 600 |
| tgcgtcgtcc cggagaacca atgtgcgatg aagcggcgcg aagagaaggc ccagaaggag | 660 |
| aaggacaaaa tgaccacttc gccgagctct cagcatggcg gcaatggcag cttggcctct | 720 |

-continued

```
ggtggcggcc aagactttgt taagaaggag attcttgacc ttatgacatg cgagccgccc    780
cagcatgcca ctattccgct actacctgat gaaatattgg ccaagtgtca agcgcgcaat    840
ataccttcct taacgtacaa tcagttggcc gttatataca agttaatttg gtaccaggat    900
ggctatgagc agccatctga agaggatctc aggcgtataa tgagtcaacc cgatgagaac    960
gagagccaaa cggacgtcag ctttcggcat ataaccgaga taaccatact cacggtccag   1020
ttgattgttg agtttgctaa aggtctacca gcgtttacaa agataccca ggaggaccag    1080 atcacgttac taaaggcctg ctcgtcgag gtgatgatgc tgcgtatggc acgacgctat    1140
gaccacagct cggactcaat attcttcgcg aataatagat catatacgcg ggattcttac    1200
aaaatggccg aatggctga taacattgaa gacctgctgc atttctgccg ccaaatgttc    1260
tcgatgaagg tggacaacgt cgaatacgcg cttctcactg ccattgtgat cttctcggac    1320
cggccgggcc tggagaaggc ccagctagtc gaagcgatcc agagctacta catcgacacg    1380
ctacgcattt atatactcaa ccgccactgc ggcgactcaa tgagcctcgt cttctacgca    1440
aagctgctct cgatcctcac cgagctgcgt acgctgggca accagaacgc cgagatgtgt    1500
ttctcactaa agctcaaaaa ccgcaaactg cccaagttcc tcgaggagat ctgggacgtt    1560
catgccatcc cgccatcggt ccagtcgcac cttcagatta cccaggagga gaacgagcgt    1620
ctcgagcggg ctgagcgtat gcgggcatcg gttgggggcg ccattaccgc cggcattgat    1680
tgcgactctg cctccacttc ggcggcggca gccgcggccc agcatcagcc tcagcctcag    1740
ccccagcccc aaccctcctc cctgacccag aacgattccc agcaccagac acagccgcag    1800
ctacaacctc agctaccacc tcagctgcaa ggtcaactgc aaccccagct ccaaccacag    1860
cttcagacgc aactccagcc acagattcaa ccacagccac agctccttcc cgtctccgct    1920
cccgtgcccg cctccgtaac cgcacctggt tccttgtccg cggtcagtac gagcagcgaa    1980
tacatgggcg gaagtgcggc cataggacca atcacgccgg caaccaccag cagtatcacg    2040
gctgccgtta ccgctagctc caccacatca gcggtaccga tgggcaacgg agttggagtc    2100
ggtgttgggg tgggcggcaa cgtcagcatg tatgcgaacg cccagacggc gatggccttg    2160
atgggtgtag ccctgcattc gcaccaagag cagcttatcg ggggagtggc ggttaagtcg    2220
gagcactcga cgactgcata g                                              2241
```

<210> SEQ ID NO 18
<211> LENGTH: 746
<212> TYPE: PRT
<213> ORGANISM: Artificial Sequence
<220> FEATURE:
<223> OTHER INFORMATION: Description of Artificial Sequence:man-made
      artificial sequence

<400> SEQUENCE: 18

```
Met Ala Pro Pro Thr Asp Val Ser Leu Gly Asp Glu Leu His Leu Asp
 1               5                  10                  15

Gly Glu Asp Val Ala Met Ala His Ala Asp Ala Leu Asp Asp Phe Asp
                20                  25                  30

Leu Asp Met Leu Gly Asp Gly Asp Ser Pro Gly Pro Gly Phe Thr Pro
            35                  40                  45

His Asp Ser Ala Pro Tyr Gly Ala Leu Asp Met Ala Asp Phe Glu Phe
        50                  55                  60

Glu Gln Met Phe Thr Asp Ala Leu Gly Ile Asp Glu Tyr Gly Gly Lys
 65                  70                  75                  80
```

-continued

```
Leu Leu Gly Thr Ser Arg Arg Ile Ser Asn Ser Ile Ser Ser Gly Arg
             85                  90                  95

Asp Asp Leu Ser Pro Ser Ser Leu Asn Gly Tyr Ser Ala Asn Glu
            100                 105                 110

Ser Cys Asp Ala Lys Lys Ser Lys Lys Gly Pro Ala Pro Arg Val Gln
            115                 120                 125

Glu Glu Leu Cys Leu Val Cys Gly Asp Arg Ala Ser Gly Tyr His Tyr
    130                 135                 140

Asn Ala Leu Thr Cys Gly Gly Cys Lys Gly Phe Phe Arg Arg Ser Val
145                 150                 155                 160

Thr Lys Ser Ala Val Tyr Cys Cys Lys Phe Gly Arg Ala Cys Glu Met
            165                 170                 175

Asp Met Tyr Met Arg Arg Lys Cys Gln Glu Cys Arg Leu Lys Lys Cys
            180                 185                 190

Leu Ala Val Gly Met Arg Pro Glu Cys Val Val Pro Glu Asn Gln Cys
            195                 200                 205

Ala Met Lys Arg Arg Glu Glu Lys Ala Gln Lys Glu Lys Asp Lys Met
    210                 215                 220

Thr Thr Ser Pro Ser Ser Gln His Gly Gly Asn Gly Ser Leu Ala Ser
225                 230                 235                 240

Gly Gly Gly Gln Asp Phe Val Lys Lys Glu Ile Leu Asp Leu Met Thr
                245                 250                 255

Cys Glu Pro Pro Gln His Ala Thr Ile Pro Leu Leu Pro Asp Glu Ile
            260                 265                 270

Leu Ala Lys Cys Gln Ala Arg Asn Ile Pro Ser Leu Thr Tyr Asn Gln
            275                 280                 285

Leu Ala Val Ile Tyr Lys Leu Ile Trp Tyr Gln Asp Gly Tyr Glu Gln
    290                 295                 300

Pro Ser Glu Glu Asp Leu Arg Arg Ile Met Ser Gln Pro Asp Glu Asn
305                 310                 315                 320

Glu Ser Gln Thr Asp Val Ser Phe Arg His Ile Thr Glu Ile Thr Ile
            325                 330                 335

Leu Thr Val Gln Leu Ile Val Glu Phe Ala Lys Gly Leu Pro Ala Phe
            340                 345                 350

Thr Lys Ile Pro Gln Glu Asp Gln Ile Thr Leu Leu Lys Ala Cys Ser
            355                 360                 365

Ser Glu Val Met Met Leu Arg Met Ala Arg Arg Tyr Asp His Ser Ser
    370                 375                 380

Asp Ser Ile Phe Phe Ala Asn Asn Arg Ser Tyr Thr Arg Asp Ser Tyr
385                 390                 395                 400

Lys Met Ala Gly Met Ala Asp Asn Ile Glu Asp Leu Leu His Phe Cys
            405                 410                 415

Arg Gln Met Phe Ser Met Lys Val Asp Asn Val Glu Tyr Ala Leu Leu
            420                 425                 430

Thr Ala Ile Val Ile Phe Ser Asp Arg Pro Gly Leu Glu Lys Ala Gln
            435                 440                 445

Leu Val Glu Ala Ile Gln Ser Tyr Tyr Ile Asp Thr Leu Arg Ile Tyr
    450                 455                 460

Ile Leu Asn Arg His Cys Gly Asp Ser Met Ser Leu Val Phe Tyr Ala
465                 470                 475                 480

Lys Leu Leu Ser Ile Leu Thr Glu Leu Arg Thr Leu Gly Asn Gln Asn
            485                 490                 495

Ala Glu Met Cys Phe Ser Leu Lys Leu Lys Asn Arg Lys Leu Pro Lys
```

```
                    500             505             510
        Phe Leu Glu Glu Ile Trp Asp Val His Ala Ile Pro Pro Ser Val Gln
                515             520             525

Ser His Leu Gln Ile Thr Gln Glu Glu Asn Glu Arg Leu Glu Arg Ala
                530             535             540

Glu Arg Met Arg Ala Ser Val Gly Gly Ala Ile Thr Ala Gly Ile Asp
        545             550             555             560

Cys Asp Ser Ala Ser Thr Ser Ala Ala Ala Ala Ala Gln His Gln
                        565             570             575

Pro Gln Pro Gln Pro Gln Pro Ser Ser Leu Thr Gln Asn Asp
                    580             585             590

Ser Gln His Gln Thr Gln Pro Gln Leu Gln Pro Gln Leu Pro Pro Gln
                595             600             605

Leu Gln Gly Gln Leu Gln Pro Gln Leu Gln Pro Gln Leu Gln Thr Gln
                610             615             620

Leu Gln Pro Gln Ile Gln Pro Gln Pro Gln Leu Leu Pro Val Ser Ala
        625             630             635             640

Pro Val Pro Ala Ser Val Thr Ala Pro Gly Ser Leu Ser Ala Val Ser
                        645             650             655

Thr Ser Ser Glu Tyr Met Gly Gly Ser Ala Ala Ile Gly Pro Ile Thr
                    660             665             670

Pro Ala Thr Thr Ser Ser Ile Thr Ala Ala Val Thr Ala Ser Ser Thr
                    675             680             685

Thr Ser Ala Val Pro Met Gly Asn Gly Val Gly Val Gly Val Gly Val
                690             695             700

Gly Gly Asn Val Ser Met Tyr Ala Asn Ala Gln Thr Ala Met Ala Leu
        705             710             715             720

Met Gly Val Ala Leu His Ser His Gln Glu Gln Leu Ile Gly Gly Val
                        725             730             735

Ala Val Lys Ser Glu His Ser Thr Thr Ala
                    740             745
```

<210> SEQ ID NO 19
<211> LENGTH: 2295
<212> TYPE: DNA
<213> ORGANISM: Artificial Sequence
<220> FEATURE:
<223> OTHER INFORMATION: Description of Artificial Sequence:man-made
      artificial sequence

<400> SEQUENCE: 19

| | | | | | |
|---|---|---|---|---|---|
| atggccccc | cgaccgatgt | cagcctgggg | gacgaactcc | acttagacgg | cgaggacgtg | 60 |
| gcgatggcgc | atgccgacgc | gctagacgat | ttcgatctgg | acatgttggg | ggacggggat | 120 |
| tccccaggtc | cggatttac | ccccacgac | tccgccccct | acggcgctct | ggatatggcc | 180 |
| gacttcgagt | ttgagcagat | gtttaccgat | gcccttggaa | ttgacgagta | cggtgggaag | 240 |
| cttctaggta | ccggcgccga | cacggaagat | gtcgtgtgct | gctcaatgtc | ttatacctgg | 300 |
| acaggctcta | aagaatatc | aaattctata | tcttcaggtc | gcgatgatct | ctcgccttcg | 360 |
| agcagcttga | acggatactc | ggcgaacgaa | agctgcgatg | cgaagaagag | caagaaggga | 420 |
| cctgcgccac | gggtgcaaga | ggagctgtgc | ctggtttgcg | gcgacagggc | ctccggctac | 480 |
| cactacaacg | ccctcacctg | tggggctgc | aaggggttct | ttcgacgcag | cgttacgaag | 540 |
| agcgccgtct | actgctgcaa | gttcgggcgc | gcctgcgaaa | tggacatgta | catgaggcga | 600 |
| aagtgtcagg | agtgccgcct | gaaaaagtgc | ctggccgtgg | gtatgcggcc | ggaatgcgtc | 660 |

```
gtcccggaga accaatgtgc gatgaagcgg cgcgaagaga aggcccagaa ggagaaggac    720
aaaatgacca cttcgccgag ctctcagcat ggcggcaatg gcagcttggc ctctggtggc    780
ggccaagact ttgttaagaa ggagattctt gaccttatga catgcgagcc gccccagcat    840
gccactattc cgctactacc tgatgaaata ttggccaagt gtcaagcgcg caatatacct    900
tccttaacgt acaatcagtt ggccgttata tacaagttaa tttggtacca ggatggctat    960
gagcagccat ctgaagagga tctcaggcgt ataatgagtc aacccgatga gaacgagagc   1020
caaacggacg tcagctttcg gcatataacc gagataacca tactcacggt ccagttgatt   1080
gttgagtttg ctaaaggtct accagcgttt acaaagatac cccaggagga ccagatcacg   1140
ttactaaagg cctgctcgtc ggaggtgatg atgctgcgta tggcacgacg ctatgaccac   1200
agctcggact caatattctt cgcgaataat agatcatata cgcgggattc ttacaaaatg   1260 gccgaatgg ctgataacat tgaagacctg ctgcatttct gccgccaaat gttctcgatg   1320
aaggtggaca acgtcgaata cgcgcttctc actgccattg tgatcttctc ggaccggccg   1380
ggcctggaga aggcccagct agtcgaagcg atccagagct actacatcga cacgctacgc   1440
atttatatac tcaaccgcca ctgcggcgac tcaatgagcc tcgtcttcta cgcaaagctg   1500
ctctcgatcc tcaccgagct gcgtacgctg gcaaccagag acgccgagat gtgtttctca   1560
ctaaagctca aaaccgcaa actgcccaag ttcctcgagg agatctggga cgttcatgcc   1620
atcccgccat cggtccagtc gcaccttcag attacccagg aggagaacga gcgtctcgag   1680
cgggctgagc gtatgcgggc atcggttggg ggcgccatta ccgccggcat tgattgcgac   1740
tctgcctcca cttcggcggc ggcagccgcg gcccagcatc agcctcagcc tcagccccag   1800
ccccaaccct cctccctgac ccagaacgat tcccagcacc agacacagcc gcagctacaa   1860
cctcagctac cacctcagct gcaaggtcaa ctgcaacccc agctccaacc acagcttcag   1920
acgcaactcc agccacagat tcaaccacag ccacagctcc ttcccgtctc cgctcccgtg   1980
cccgcctccg taaccgcacc tggttccttg tccgcggtca gtacgagcag cgaatacatg   2040
ggcggaagtg cggccatagg accaatcacg ccggcaacca ccagcagtat cacggctgcc   2100
gttaccgcta gctccaccac atcagcggta ccgatgggca acggagttgg agtcggtgtt   2160
ggggtgggcg gcaacgtcag catgtatgcg aacgcccaga cggcgatggc cttgatgggt   2220
gtagccctgc attcgcacca agagcagctt atcggggag tggcggttaa gtcggagcac   2280
tcgacgactg catag                                                    2295
```

<210> SEQ ID NO 20
<211> LENGTH: 764
<212> TYPE: PRT
<213> ORGANISM: Artificial Sequence
<220> FEATURE:
<223> OTHER INFORMATION: Description of Artificial Sequence:man-made
      artificial sequence

<400> SEQUENCE: 20

```
Met Ala Pro Pro Thr Asp Val Ser Leu Gly Asp Glu Leu His Leu Asp
 1               5                  10                  15

Gly Glu Asp Val Ala Met Ala His Ala Asp Ala Leu Asp Asp Phe Asp
             20                  25                  30

Leu Asp Met Leu Gly Asp Gly Asp Ser Pro Gly Pro Gly Phe Thr Pro
         35                  40                  45

His Asp Ser Ala Pro Tyr Gly Ala Leu Asp Met Ala Asp Phe Glu Phe
     50                  55                  60
```

```
Glu Gln Met Phe Thr Asp Ala Leu Gly Ile Asp Glu Tyr Gly Gly Lys
 65                  70                  75                  80

Leu Leu Gly Thr Gly Ala Asp Thr Glu Asp Val Val Cys Cys Ser Met
                 85                  90                  95

Ser Tyr Thr Trp Thr Gly Ser Arg Arg Ile Ser Asn Ser Ile Ser Ser
                100                 105                 110

Gly Arg Asp Asp Leu Ser Pro Ser Ser Leu Asn Gly Tyr Ser Ala
            115                 120                 125

Asn Glu Ser Cys Asp Ala Lys Lys Ser Lys Lys Gly Pro Ala Pro Arg
    130                 135                 140

Val Gln Glu Glu Leu Cys Leu Val Cys Gly Asp Arg Ala Ser Gly Tyr
145                 150                 155                 160

His Tyr Asn Ala Leu Thr Cys Gly Gly Cys Lys Gly Phe Phe Arg Arg
                165                 170                 175

Ser Val Thr Lys Ser Ala Val Tyr Cys Cys Lys Phe Gly Arg Ala Cys
            180                 185                 190

Glu Met Asp Met Tyr Met Arg Arg Lys Cys Gln Glu Cys Arg Leu Lys
    195                 200                 205

Lys Cys Leu Ala Val Gly Met Arg Pro Glu Cys Val Val Pro Glu Asn
210                 215                 220

Gln Cys Ala Met Lys Arg Arg Glu Glu Lys Ala Gln Lys Glu Lys Asp
225                 230                 235                 240

Lys Met Thr Thr Ser Pro Ser Ser Gln His Gly Gly Asn Gly Ser Leu
                245                 250                 255

Ala Ser Gly Gly Gly Gln Asp Phe Val Lys Lys Glu Ile Leu Asp Leu
            260                 265                 270

Met Thr Cys Glu Pro Pro Gln His Ala Thr Ile Pro Leu Leu Pro Asp
        275                 280                 285

Glu Ile Leu Ala Lys Cys Gln Ala Arg Asn Ile Pro Ser Leu Thr Tyr
    290                 295                 300

Asn Gln Leu Ala Val Ile Tyr Lys Leu Ile Trp Tyr Gln Asp Gly Tyr
305                 310                 315                 320

Glu Gln Pro Ser Glu Glu Asp Leu Arg Arg Ile Met Ser Gln Pro Asp
                325                 330                 335

Glu Asn Glu Ser Gln Thr Asp Val Ser Phe Arg His Ile Thr Glu Ile
            340                 345                 350

Thr Ile Leu Thr Val Gln Leu Ile Val Glu Phe Ala Lys Gly Leu Pro
        355                 360                 365

Ala Phe Thr Lys Ile Pro Gln Glu Asp Gln Ile Thr Leu Leu Lys Ala
    370                 375                 380

Cys Ser Ser Glu Val Met Met Leu Arg Met Ala Arg Arg Tyr Asp His
385                 390                 395                 400

Ser Ser Asp Ser Ile Phe Ala Asn Asn Arg Ser Tyr Thr Arg Asp
                405                 410                 415

Ser Tyr Lys Met Ala Gly Met Ala Asp Asn Ile Glu Asp Leu Leu His
            420                 425                 430

Phe Cys Arg Gln Met Phe Ser Met Lys Val Asp Asn Val Glu Tyr Ala
    435                 440                 445

Leu Leu Thr Ala Ile Val Ile Phe Ser Asp Arg Pro Gly Leu Glu Lys
450                 455                 460

Ala Gln Leu Val Glu Ala Ile Gln Ser Tyr Tyr Ile Asp Thr Leu Arg
465                 470                 475                 480
```

```
Ile Tyr Ile Leu Asn Arg His Cys Gly Asp Ser Met Ser Leu Val Phe
                485                 490                 495
Tyr Ala Lys Leu Leu Ser Ile Leu Thr Glu Leu Arg Thr Leu Gly Asn
            500                 505                 510
Gln Asn Ala Glu Met Cys Phe Ser Leu Lys Leu Lys Asn Arg Lys Leu
        515                 520                 525
Pro Lys Phe Leu Glu Glu Ile Trp Asp Val His Ala Ile Pro Pro Ser
    530                 535                 540
Val Gln Ser His Leu Gln Ile Thr Gln Glu Glu Asn Glu Arg Leu Glu
545                 550                 555                 560
Arg Ala Glu Arg Met Arg Ala Ser Val Gly Gly Ala Ile Thr Ala Gly
                565                 570                 575
Ile Asp Cys Asp Ser Ala Ser Thr Ser Ala Ala Ala Ala Ala Ala Gln
            580                 585                 590
His Gln Pro Gln Pro Gln Pro Gln Pro Ser Ser Leu Thr Gln
        595                 600                 605
Asn Asp Ser Gln His Gln Thr Gln Pro Gln Leu Gln Pro Gln Leu Pro
    610                 615                 620
Pro Gln Leu Gln Gly Gln Leu Gln Pro Gln Leu Gln Pro Gln Leu Gln
625                 630                 635                 640
Thr Gln Leu Gln Pro Gln Ile Gln Pro Gln Pro Gln Leu Leu Pro Val
                645                 650                 655
Ser Ala Pro Val Pro Ala Ser Val Thr Ala Pro Gly Ser Leu Ser Ala
            660                 665                 670
Val Ser Thr Ser Ser Glu Tyr Met Gly Gly Ser Ala Ala Ile Gly Pro
        675                 680                 685
Ile Thr Pro Ala Thr Thr Ser Ser Ile Thr Ala Ala Val Thr Ala Ser
    690                 695                 700
Ser Thr Thr Ser Ala Val Pro Met Gly Asn Gly Val Gly Val Gly Val
705                 710                 715                 720
Gly Val Gly Gly Asn Val Ser Met Tyr Ala Asn Ala Gln Thr Ala Met
                725                 730                 735
Ala Leu Met Gly Val Ala Leu His Ser His Gln Glu Gln Leu Ile Gly
            740                 745                 750
Gly Val Ala Val Lys Ser Glu His Ser Thr Thr Ala
        755                 760
```

<210> SEQ ID NO 21
<211> LENGTH: 2301
<212> TYPE: DNA
<213> ORGANISM: Artificial Sequence
<220> FEATURE:
<223> OTHER INFORMATION: Description of Artificial Sequence:man-made
      artificial sequence

<400> SEQUENCE: 21

```
atggccccc cgaccgatgt cagcctgggg gacgaactcc acttagacgg cgaggacgtg      60
gcgatggcgc atgccgacgc gctagacgat ttcgatctgg acatgttggg ggacggggat    120
tccccaggtc cgggatttac cccccacgac tccgcccccct acggcgctct ggatatggcc   180
gacttcgagt ttgagcagat gtttaccgat gcccttggaa ttgacgagta cggtgggaag   240
cttctaggta ccggcgccga cacggaagat gtcgtgtgct gctgatgatc aatgtcttat   300
acctggacag gctctagaag aatatcaaat tctatatctt caggtcgcga tgatctctcg   360
ccttcgagca gcttgaacgg atactcggcg aacgaaagct gcgatgcgaa gaagagcaag   420
```

-continued

```
aagggacctg cgccacgggt gcaagaggag ctgtgcctgg tttgcggcga cagggcctcc      480
ggctaccact acaacgccct cacctgtggg ggctgcaagg ggttctttcg acgcagcgtt      540
acgaagagcg ccgtctactg ctgcaagttc gggcgcgcct gcgaaatgga catgtacatg      600
aggcgaaagt gtcaggagtg ccgcctgaaa aagtgcctgg ccgtgggtat gcggccggaa      660
tgcgtcgtcc cggagaacca atgtgcgatg aagcggcgcg aagagaaggc ccagaaggag      720
aaggacaaaa tgaccacttc gccgagctct cagcatggcg gcaatggcag cttggcctct      780
ggtggcggcc aagactttgt taagaaggag attcttgacc ttatgacatg cgagccgccc      840
cagcatgcca ctattccgct actacctgat gaaatattgg ccaagtgtca agcgcgcaat      900
ataccttcct aacgtacaa tcagttggcc gttatataca agttaatttg gtaccaggat       960
ggctatgagc agccatctga agaggatctc aggcgtataa tgagtcaacc cgatgagaac     1020
gagagccaaa cggacgtcag ctttcggcat ataaccgaga taaccatact cacggtccag     1080
ttgattgttg agtttgctaa aggtctacca gcgtttacaa agataccca ggaggaccag      1140 atcacgttac taaaggcctg ctcgtcgag gtgatgatgc tgcgtatggc acgacgctat      1200
gaccacagct cggactcaat attcttcgcg aataatagat catatacgcg ggattcttac     1260
aaaatggccg gaatggctga taacattgaa gacctgctgc atttctgccg ccaaatgttc     1320
tcgatgaagg tggacaacgt cgaatacgcg cttctcactg ccattgtgat cttctcggac     1380
cggccgggcc tggagaaggc ccagctagtc gaagcgatcc agagctacta catcgacacg     1440
ctacgcattt atatactcaa ccgccactgc ggcgactcaa tgagcctcgt cttctacgca     1500
aagctgctct cgatcctcac cgagctgcgt acgctgggca accagaacgc cgagatgtgt     1560
ttctcactaa agctcaaaaa ccgcaaactg cccaagttcc tcgaggagat ctgggacgtt     1620
catgccatcc cgccatcggt ccagtcgcac cttcagatta cccaggagga gaacgagcgt     1680
ctcgagcggg ctgagcgtat gcgggcatcg gttgggggcg ccattaccgc cggcattgat     1740
tgcgactctg cctccacttc ggcggcggca gccgcggccc agcatcagcc tcagcctcag     1800
ccccagcccc aaccctcctc cctgacccag aacgattccc agcaccagac acagccgcag     1860
ctacaacctc agctaccacc tcagctgcaa ggtcaactgc aaccccagct ccaaccacag     1920
cttcagacgc aactccagcc acagattcaa ccacagccac agctccttcc cgtctccgct     1980
cccgtgcccg cctccgtaac cgcacctggt tccttgtccg cggtcagtac gagcagcgaa     2040
tacatgggcg gaagtgcggc cataggacca atcacgccgg caaccaccag cagtatcacg     2100
gctgccgtta ccgctagctc caccacatca gcggtaccga tgggcaacgg agttggagtc     2160
ggtgttgggg tgggcggcaa cgtcagcatg tatgcgaacg cccagacggc gatggccttg     2220
atgggtgtag ccctgcattc gcaccaagag cagcttatcg ggggagtggc ggttaagtcg     2280
gagcactcga cgactgcata g                                               2301
```

<210> SEQ ID NO 22
<211> LENGTH: 94
<212> TYPE: PRT
<213> ORGANISM: Artificial Sequence
<220> FEATURE:
<223> OTHER INFORMATION: Description of Artificial Sequence:man-made
      artificial sequence

<400> SEQUENCE: 22

Met Ala Pro Pro Thr Asp Val Ser Leu Gly Asp Glu Leu His Leu Asp
 1               5                  10                  15

Gly Glu Asp Val Ala Met Ala His Ala Asp Ala Leu Asp Asp Phe Asp

-continued

```
                 20                  25                  30

Leu Asp Met Leu Gly Asp Gly Asp Ser Pro Gly Pro Gly Phe Thr Pro
            35                  40                  45

His Asp Ser Ala Pro Tyr Gly Ala Leu Asp Met Ala Asp Phe Glu Phe
     50                  55                  60

Glu Gln Met Phe Thr Asp Ala Leu Gly Ile Asp Glu Tyr Gly Gly Lys
 65                  70                  75                  80

Leu Leu Gly Thr Gly Ala Asp Thr Glu Asp Val Val Cys Cys
                85                  90

<210> SEQ ID NO 23
<211> LENGTH: 5
<212> TYPE: PRT
<213> ORGANISM: Drosophila

<400> SEQUENCE: 23

Glu Gly Cys Lys Gly
 1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence:man-made
      artificial sequence

<400> SEQUENCE: 24

Gly Ser Cys Lys Val
 1               5
```